US012766141B2

(12) United States Patent
Eguchi et al.

(10) Patent No.: US 12,766,141 B2
(45) **Date of Patent: *Oct. 20, 2026**

(54) MEDICAMENT FOR TREATING CANCER COMPRISING OPTICALLY ACTIVE AZABICYCLO RING DERIVATIVE

(71) Applicant: Sumitomo Pharma Co., Ltd., Osaka (JP)

(72) Inventors: Ken Eguchi, Osaka (JP); Akinobu Watanabe, Chuo-ku (JP); Taeko Kusuda, Osaka (JP); Mami Inoue, Osaka (JP); Takafumi Shimizu, Osaka (JP); Mariko Matsubara, Chuo-ku (JP); Takahiro Kuwaki, Chuo-ku (JP); Matthew Hitron, Marlborough, MA (US); Hongliang Cai, Marlborough, MA (US); Bo Xu, Marlborough, MA (US); Emily Brooks, Marlborough, MA (US); Curtis Allred, Marlborough, MA (US); Vishnu Peddagali, Marlborough, MA (US)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/095,723

(22) Filed: Mar. 31, 2025

(65) Prior Publication Data

US 2025/0295663 A1 Sep. 25, 2025
US 2026/0248787 A9 Aug. 27, 2026

Related U.S. Application Data

(63) Continuation of application No. 19/114,480, filed as application No. PCT/JP2024/038683 on Oct. 30, 2024.

(60) Provisional application No. 63/709,204, filed on Oct. 18, 2024, provisional application No. 63/658,920, filed on Jun. 12, 2024, provisional application No. 63/645,182, filed on May 10, 2024, provisional application No. 63/604,527, filed on Nov. 30, 2023, provisional application No. 63/594,442, filed on Oct. 31, 2023.

(51) Int. Cl.

| | |
|---|---|
| ***A61K 31/506*** | (2006.01) |
| ***A61K 9/00*** | (2006.01) |
| ***A61K 31/497*** | (2006.01) |
| ***A61K 31/635*** | (2006.01) |
| ***A61K 31/704*** | (2006.01) |
| ***A61K 31/706*** | (2006.01) |
| ***A61K 31/7068*** | (2006.01) |
| ***A61P 35/02*** | (2006.01) |

(52) U.S. Cl.
CPC .......... *A61K 31/506* (2013.01); *A61K 9/0053* (2013.01); *A61K 31/497* (2013.01); *A61K 31/635* (2013.01); *A61K 31/704* (2013.01); *A61K 31/706* (2013.01); *A61K 31/7068* (2013.01); *A61P 35/02* (2018.01)

(58) Field of Classification Search
CPC .............................. A61K 31/506; A61P 35/02
See application file for complete search history.

(56) References Cited

U.S. PATENT DOCUMENTS 11,369,605 B2 * 6/2022 Kamioka ............. A61K 31/506
2022/0288072 A1 * 9/2022 Kamioka ................ A61P 43/00

FOREIGN PATENT DOCUMENTS

WO WO-2022086986 A1 * 4/2022 ......... A61K 31/5375

OTHER PUBLICATIONS

K. Eguchi, et al. (Blood 2021; 138 (Supplement 1): 3339, doi.org/10.1182/blood-2021-152050. (Year: 2021).*
S. Chakraborty, et al. Ecancermedicalscience. 2012, 14;6:ed16. doi: 10.3332/ecancer.2012.ed16. (Year: 2012).*
A. Zafar, et al. Med Res Rev. 2021;41:961-1021, DOI: 10.1002/med.21750. (Year: 2021).*
Nih, PubChem, Jun. 27, 2020, https://pubchem.ncbi.nlm.nih.gov/compound/Enzomenib. (Year: 2020).*
Reagan-Shaw et al. The FASEB Journal, 2007, vol. 22, 659-661. (Year: 2007).*
Look "Oncogenic Transcription Factors in the Human Acute Leukemias", www.sciencemag.org, Science, vol. 278 (5340): Nov. 1997, pp. 1059-1064.
Yokoyama et al. "The Menin Tumor Suppressor Protein Is an Essential Oncogenic Cofactor for MLL-Associated Leukemogenesis", Cell, vol. 123 (2): Oct. 21, 2005, Copyright © 2005 by Elsevier Inc. DOI 10.1016/j.cell.2005.09.025, pp. 207-218.
Yokoyama et al. "Menin Critically Links MLL Proteins with LEDGF on Cancer-Associated Target Genes", Cancer Cell, vol. 14 (1), Jul. 2008 © 2008 Elsevier Inc., pp. 36-46.
Malik et al. "Targeting the MLL complex in castration-resistant prostate cancer", vol. 21 | No. 4 | Apr. 2015 nature medicine, pp. 344-352.

(Continued)

*Primary Examiner* — James H Alstrum-Acevedo
*Assistant Examiner* — Manahil Mirghani Ali Abdalhameed
(74) *Attorney, Agent, or Firm* — Oblon, McClelland, Maier & Neustadt, L.L.P.

(57) ABSTRACT

The present invention relates to suitable usage, dosage, and use of an optically active azabicyclo ring derivative useful as a medicament, or a pharmaceutically acceptable salt thereof, and a pharmaceutical composition comprising it.

7 Claims, 13 Drawing Sheets

(56) References Cited

OTHER PUBLICATIONS

Imachi et al. "Menin, a product of the MENI gene, binds to estrogen receptor to enhance its activity in breast cancer cells: possibility of a novel predictive factor for tamoxifen resistance", Breast Cancer Res Treat (2010) 122 (2): pp. 395-407.

Svoboda et al. "Tumorigenicity of Ewing sarcoma is critically dependent on the trithorax proteins MLL1 and menin", Oncotarget, 2017, vol. 8, (No. 1), pp. 458-471.

New Releases of Sumitomo Pharma (Dec. 9, 2024; https://news.us.sumitomo-pharma.com/) New Data on Nuvisertib and Enzomenib at the 2024 American Society of Hematology Annual Meeting pp. 1-5.

616.ACUTE Myeloid Leukemias: Investigational Drug and Cellular Therapies, The 66$^{th}$ ASH Annual Meeting Abstracts Oral Abstracts, Blood 144 (2024) pp. 213-216.

* cited by examiner

MEDICAMENT FOR TREATING CANCER COMPRISING OPTICALLY ACTIVE AZABICYCLO RING DERIVATIVE

CROSS-REFERENCE TO RELATED APPLICATIONS

The present application is a continuation of U.S. application Ser. No. 19/114,480, filed Mar. 24, 2025, which is a National Stage of International Application PCT/JP2024/038683, filed on Oct. 30, 2024, which is based on and claims the benefits of priority to U.S. Provisional Applications No. 63/594,442, filed Oct. 31, 2023, No. 63/604,527, filed on Nov. 30, 2023, No. 63/645,182, filed May 10, 2024, No. 63/658,920, filed Jun. 12, 2024, and No. 63/709,204, filed Oct. 18, 2024. The entire contents of all of the above applications are incorporated herein by reference.

TECHNICAL FIELD

The present invention relates to suitable usage, dosage, and use of an optically active azabicyclo ring derivative useful as a medicament, or a pharmaceutically acceptable salt thereof, and a pharmaceutical composition comprising it.

BACKGROUND ART

MLL leukemia is a disease that accounts for about 6 to 7% of acute myeloid leukemia (AML) and acute lymphoblastic leukemia (ALL), and about 1100 people are newly diagnosed with MLL leukemia each year in America. It has been reported that major fusion partner genes that cause MLL leukemia are likely to be AF9, ELL, ENL, AF10, and AF6 in AML, and AF4, ENL, and AF9 in ALL (Non-patent literature 1).

It is inferred that a MLL fusion protein fused with a fusion partner gene can cause unrestrained proliferation of undifferentiated hematopoietic cells to lead to leukemia (Non-patent literature 2). It is reported that a MLL fusion protein firstly binds to menin to form a complex. Accordingly, it is expected that canceration caused by a MLL fusion protein can be prevented by inhibiting the first binding between a MLL fusion protein and menin (Non-patent literature 3).

It is reported that MLL acts as an activation cofactor of an androgen signal in prostate cancer. Accordingly, it is expected that a small molecular inhibitor which is targeted to inhibiting the binding between menin and a MLL fusion protein is useful as a medicament for treating the cancer (Non-patent literature 4).

It is reported that menin acts as an activation cofactor of an estrogen signal in breast cancer. Accordingly, it is expected that a small molecular inhibitor which is targeted to inhibiting the binding between menin and a MLL fusion protein is useful as a medicament of the cancer (Non-patent literature 5).

It is reported that menin or MLL is important for tumor progression in Ewing's sarcoma, liver cancer, and p53 gain-of-function mutation cancer, and it is expected that a small molecular inhibitor which is targeted to inhibiting the binding between menin and a MLL fusion protein is useful as a medicament of the cancers (Non-patent literature 6).

Recently, an optically active azabicyclo ring derivative which is targeted to inhibiting the binding between menin and a MLL fusion protein was reported in Patent Literature 1.

CITATION LIST

Patent Literature

[PL 1] WO 2020/045334

Non-Patent Literature

[NPL 1] Look A. T, Science, 278 (5340): 1059-1064 (1997)

[NPL 2] Yokoyama A, et al., Cell 123 (2): 207-218 (2005)

[NPL 3] Yokoyama A, et al., Cancer Cell. 14 (1): 34-46 (2008)

[NPL 4] Malik, R. et al., Nature Medicine. 21 (4): 344-352 (2015)

[NPL 5] Imachi, H et al., Breast Cancer Res Treat. 122 (2): 395-407 (2010)

[NPL 6] Svoboda, L. K. et al., Oncotargrt. 8 (1): 458-471 (2017)

SUMMARY OF INVENTION

Technical Problem

The purpose of the present invention is to provide an invention related to the usage and dosage of an optically active azabicyclo ring derivative that exhibits excellent anticancer effects by inhibiting the binding between menin and a MLL fusion protein, and to provide a useful therapeutic drug and method for treating tumors having a specific gene mutation with the derivative and a combination drug.

In more detail, the present inventors provide technology related to a medicament comprising 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (hereinafter, it may be referred to as "free form" or "free form of the present compound") or a pharmaceutically acceptable salt thereof (hereinafter, the both may be referred to as "the present compound" or "the compound of the present invention").

Solution to Problem

The present inventors have extensively studied to reach the above purpose, and then have found that a medicament comprising 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide or a pharmaceutically acceptable salt thereof, or a hydrate or solvate thereof exhibits excellent anticancer effects together with high safety at specific usage and dosage. In addition, the present inventors have also found that the anticancer effect can be further enhanced by using a combination drug in addition to the above-mentioned medicament. Based upon the findings, the present invention has been achieved.

Accordingly, the present invention is described as follows:

(Item 1)

A medicament comprising 5-fluoro-2-[(4-{7-[(1S,3,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (hereinafter, it may be referred to as "free form") or a pharmaceutically acceptable salt thereof, or a hydrate or solvate thereof as an active ingredient, for treating or preventing a cancer, which is orally administered to a subject in need thereof.

(Item 2)

The medicament of Item 1, which is orally administered to a subject in need thereof once a day.

(Item 3)

The medicament of Item 1, which is orally administered to a subject in need thereof twice a day.

(Item 4)

The medicament of any one of Items 1 to 3, wherein one dose of the active ingredient is 40 mg converted to the free form.

(Item 5)

The medicament of any one of Items 1 to 3, wherein one dose of the active ingredient is 60 mg converted to the free form.

(Item 6)

The medicament of any one of Items 1 to 3, wherein one dose of the active ingredient is 80 mg converted to the free form.

(Item 7)

The medicament of any one of Items 1 to 3, wherein one dose of the active ingredient is 100 mg converted to the free form.

(Item 8)

The medicament of any one of Items 1 to 3, wherein one dose of the active ingredient is 120 mg converted to the free form.

(Item 9)

The medicament of any one of Items 1 to 3, wherein one dose of the active ingredient is 140 mg converted to the free (Item 10)

The medicament of any one of Items 1 to 3, wherein one dose of the active ingredient is 180 mg converted to the free form.

(Item 11)

The medicament of any one of Items 1 to 3, wherein one dose of the active ingredient is 200 mg converted to the free form.

(Item 12)

The medicament of any one of Items 1 to 3, wherein one dose of the active ingredient is 220 mg converted to the free form.

(Item 13)

The medicament of any one of Items 1 to 3, wherein one dose of the active ingredient is 240 mg converted to the free form.

(Item 14)

The medicament of any one of Items 1 to 3, wherein one dose of the active ingredient is 260 mg converted to the free (Item 15)

The medicament of any one of Items 1 to 3, wherein one dose of the active ingredient is 280 mg converted to the free form.

(Item 16)

The medicament of any one of Items 1 to 3, wherein one dose of the active ingredient is 300 mg converted to the free form.

(Item 17)

The medicament of any one of Items 1 to 3, wherein one dose of the active ingredient is 320 mg converted to the free form.

(Item 18)

The medicament of any one of Items 1 to 3, wherein one dose of the active ingredient is 340 mg converted to the free form.

(Item 19)

The medicament of any one of Items 1 to 3, wherein one dose of the active ingredient is 360 mg converted to the free (Item 20)

The medicament of any one of Items 1 to 3, wherein one dose of the active ingredient is 380 mg converted to the free form.

(Item 21)

The medicament of any one of Items 1 to 3, wherein one dose of the active ingredient is 400 mg converted to the free form.

(Item 22)

The medicament of any one of Items 1 to 3, wherein one dose of the active ingredient is 500 mg converted to the free form.

(Item 23)

The medicament of any one of Items 1 to 3, wherein one dose of the active ingredient is 600 mg converted to the free form.

(Item 24)

The medicament of any one of Items 1 to 23, which is used in combination with a different drug or a pharmaceutically acceptable salt thereof, wherein the different drug is at least one drug selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(Item 25)

The medicament of any one of Items 1 to 23, which is used in combination with a different drug or a pharmaceutically acceptable salt thereof, wherein the different drug is at least one drug selected from (1) venetoclax and azacitidine (2) cytarabine and daunorubicin, and (3) gilteritinib.

(Item 26)

The medicament of any one of Items 1 to 23, which is administered in combination with gilteritinib once a day.

(Item 27)

The medicament of any one of Items 1 to 23, which is administered in combination with 120 mg of gilteritinib.

(Item 28)

The medicament of any one of Items 1 to 27, wherein the cancer is leukemia, polycythemia vera, malignant lymphoma, B-cell lymphoma, myeloma, brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item 29)

The medicament of any one of Items 1 to 27, wherein the cancer is leukemia, B-cell lymphoma, neuroblastoma, or prostate cancer.

(Item 30)

The medicament of any one of Items 1 to 27, wherein the cancer is leukemia.

(Item 31)

The medicament of any one of Items 28 to 30, wherein the leukemia is acute leukemia, chronic lymphocytic leukemia, or chronic myeloid leukemia.

(Item 32)

The medicament of Item 31, wherein the acute leukemia is MLL acute leukemia, MLL partial tandem duplicate acute leukemia, or NPM1 mutated acute leukemia.

(Item 33)

The medicament of Item 31, wherein the acute leukemia is MLL acute leukemia or NPM1 mutated acute leukemia.

(Item 34)

The medicament of Item 31, wherein the acute leukemia is acute myeloid leukemia with MLL rearrangement.

(Item 35)

The medicament of Item 31, wherein the acute leukemia is relapsed or refractory acute myeloid leukemia with MLL rearrangement.

(Item 36)

The medicament of Item 31, wherein the acute leukemia is acute lymphoid leukemia with MLL rearrangement.

(Item 37)

The medicament of Item 31, wherein the acute leukemia is relapsed or refractory acute lymphoid leukemia with MLL rearrangement.

(Item 38)

The medicament of Item 31, wherein the acute leukemia is acute myeloid leukemia with NPM1 mutation.

(Item 39)

The medicament of Item 31, wherein the acute leukemia is relapsed or refractory acute myeloid leukemia with NPM1 mutation.

(Item 40)

The medicament of Item 31, wherein the acute leukemia is leukemia accompanied by high expression of HOXa gene cluster or MEIS gene cluster.

(Item 41)

The medicament of any one of Items 1 to 27, wherein the cancer is tumor accompanied by p53 gain-of-function mutation.

(Item 42)

The medicament of any one of Items 1 to 27, wherein the cancer exhibits at least one genetic abnormality selected from NPM1 gene mutation, DNMT3A gene mutation, FLT gene mutation, and MLL translocation.

(Item 43)

The medicament of any one of Items 1 to 27, wherein the cancer exhibits at least one genetic abnormality selected from NPM1 gene mutation, FLT gene mutation, and MLL translocation.

(Item 44)

The medicament of any one of Items 1 to 27, wherein the cancer exhibits at least one genetic abnormality selected from NPM1 gene mutation and MLL translocation.

(Item 45)

The medicament of any one of Items 1 to 44, which is administered to a subject having at least one genetic abnormality selected from NPM1 gene mutation, DNMT3A gene mutation, FLT gene mutation, and MLL translocation.

(Item 46)

The medicament of any one of Items 1 to 44, which is administered to a subject having at least one genetic abnormality selected from NPM1 gene mutation and MLL translocation.

(Item 47)

The medicament of any one of Items 1 to 44, which is administered to a subject having NPM1 gene mutation.

(Item 48)

The medicament of Item 47, wherein the subject having NPM1 gene mutation is determined based on (1) a step of detecting the NPM1 gene mutation in cancer cells obtained from the subject, and (2) a step of determining presence/absence of the NPM1 gene mutation detected in step (1).

(Item 49)

The medicament of any one of Items 1 to 44, which is administered to a subject having MLL translocation.

(Item 50)

The medicament of Item 49, wherein the subject having MLL translocation is determined based on (1) a step of detecting the MLL translocation in cancer cells obtained from the subject, and (2) a step of determining presence/absence of the MLL translocation detected in step (1).

(Item 51)

The medicament of any one of Items 1 to 44, which is administered to a subject having FLT gene mutation.

(Item 52)

The medicament of Item 51, wherein the subject having FLT gene mutation is determined based on (1) a step of detecting the FLT gene mutation in cancer cells obtained from the subject, and (2) a step of determining presence/absence of the FLT gene mutation detected in step (1).

(Item 53)

The medicament of any one of Items 1 to 44, which is administered to a subject having DNMT3A gene mutation.

(Item 54)

The medicament of Item 53, wherein the subject having DNMT3A gene mutation is determined based on (1) a step of detecting the DNMT3A gene mutation in cancer cells obtained from the subject, and (2) a step of determining presence/absence of the DNMT3A gene mutation detected in step (1).

In addition, the present invention is described as follows:

(Item A1)

Use of 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (hereinafter, it may be referred to as "free form") or a pharmaceutically acceptable salt thereof, or a hydrate or solvate thereof as an active ingredient, in the manufacture of a medicament for treating or preventing a cancer, said medicament is orally administered to a subject in need thereof.

(Item A2)

The use of Item A1, wherein the medicament is orally administered to a subject in need thereof once a day.

(Item A3)

The use of Item A1, wherein the medicament is orally administered to a subject in need thereof twice a day.

(Item A4)

The use of any one of Items A1 to A3, wherein one dose of the active ingredient is 40 mg converted to the free form.

(Item A5)

The use of any one of Items A1 to A3, wherein one dose of the active ingredient is 60 mg converted to the free form.

(Item A6)

The use of any one of Items A1 to A3, wherein one dose of the active ingredient is 80 mg converted to the free form.

(Item A7)

The use of any one of Items A1 to A3, wherein one dose of the active ingredient is 100 mg converted to the free form.

(Item A8)

The use of any one of Items A1 to A3, wherein one dose of the active ingredient is 120 mg converted to the free form.

(Item A9)

The use of any one of Items A1 to A3, wherein one dose of the active ingredient is 140 mg converted to the free form.

(Item A10)

The use of any one of Items A1 to A3, wherein one dose of the active ingredient is 180 mg converted to the free form.

(Item A11)

The use of any one of Items A1 to A3, wherein one dose of the active ingredient is 200 mg converted to the free form.

(Item A12)

The use of any one of Items A1 to A3, wherein one dose of the active ingredient is 220 mg converted to the free form.

(Item A13)

The use of any one of Items A1 to A3, wherein one dose of the active ingredient is 240 mg converted to the free form.

(Item A14)

The use of any one of Items A1 to A3, wherein one dose of the active ingredient is 260 mg converted to the free form.

(Item A15)

The use of any one of Items A1 to A3, wherein one dose of the active ingredient is 280 mg converted to the free form.

(Item A16)

The use of any one of Items A1 to A3, wherein one dose of the active ingredient is 300 mg converted to the free form.

(Item A17)

The use of any one of Items A1 to A3, wherein one dose of the active ingredient is 320 mg converted to the free form.

(Item A18)

The use of any one of Items A1 to A3, wherein one dose of the active ingredient is 340 mg converted to the free form.

(Item A19)

The use of any one of Items A1 to A3, wherein one dose of the active ingredient is 360 mg converted to the free form.

(Item A20)

The use of any one of Items A1 to A3, wherein one dose of the active ingredient is 380 mg converted to the free form.

(Item A21)

The use of any one of Items A1 to A3, wherein one dose of the active ingredient is 400 mg converted to the free form.

(Item A22)

The use of any one of Items A1 to A3, wherein one dose of the active ingredient is 500 mg converted to the free form.

(Item A23)

The use of any one of Items A1 to A3, wherein one dose of the active ingredient is 600 mg converted to the free form.

(Item A24)

The use of any one of Items A1 to A23, wherein the medicament is used in combination with a different drug or a pharmaceutically acceptable salt thereof, wherein the different drug is at least one drug selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(Item A25)

The use of any one of Items A1 to A23, wherein the medicament is used in combination with a different drug or a pharmaceutically acceptable salt thereof, wherein the different drug is at least one drug selected from (1) venetoclax and azacitidine (2) cytarabine and daunorubicin, and (3) gilteritinib.

(Item A26)

The use of any one of Items A1 to A23, wherein the medicament is administered in combination with gilteritinib once a day.

(Item A27)

The use of any one of Items A1 to A23, wherein the medicament is administered in combination with 120 mg of gilteritinib.

(Item A28)

The use of any one of Items A1 to A27, wherein the cancer is leukemia, polycythemia vera, malignant lymphoma, B-cell lymphoma, myeloma, brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item A29)

The use of any one of Items A1 to A27, wherein the cancer is leukemia, B-cell lymphoma, neuroblastoma, or prostate cancer.

(Item A30)

The use of any one of Items A1 to A27, wherein the cancer is leukemia.

(Item A31)

The use of any one of Items A28 to A30, wherein the leukemia is acute leukemia, chronic lymphocytic leukemia, or chronic myeloid leukemia.

(Item A32)

The use of Item A31, wherein the acute leukemia is MLL acute leukemia, MLL partial tandem duplicate acute leukemia, or NPM1 mutated acute leukemia.

(Item A33)

The use of Item A31, wherein the acute leukemia is MLL acute leukemia or NPM1 mutated acute leukemia.

(Item A34)

The use of Item A31, wherein the acute leukemia is acute myeloid leukemia with MLL rearrangement.

(Item A35)

The use of Item A31, wherein the acute leukemia is relapsed or refractory acute myeloid leukemia with MLL rearrangement.

(Item A36)

The use of Item A31, wherein the acute leukemia is acute lymphoid leukemia with MLL rearrangement.

(Item A37)

The use of Item A31, wherein the acute leukemia is relapsed or refractory acute lymphoid leukemia with MLL rearrangement.

(Item A38)

The use of Item A31, wherein the acute leukemia is acute myeloid leukemia with NPM1 mutation.

(Item A39)

The use of Item A31, wherein the acute leukemia is relapsed or refractory acute myeloid leukemia with NPM1 mutation.

(Item A40)

The use of Item A31, wherein the acute leukemia is leukemia accompanied by high expression of HOXa gene cluster or MEIS gene cluster.

(Item A41)

The use of any one of Items A1 to A27, wherein the cancer is tumor accompanied by p53 gain-of-function mutation.

(Item A42)

The use of any one of Items A1 to A27, wherein the cancer exhibits at least one genetic abnormality selected from NPM1 gene mutation, DNMT3A gene mutation, FLT gene mutation, and MLL translocation.

(Item A43)

The use of any one of Items A1 to A27, wherein the cancer exhibits at least one genetic abnormality selected from NPM1 gene mutation, FLT gene mutation, and MLL translocation.

(Item A44)

The use of any one of Items A1 to A27, wherein the cancer exhibits at least one genetic abnormality selected from NPM1 gene mutation and MLL translocation.

(Item A45)

The use of any one of Items A1 to A44, wherein the medicament is administered to a subject having at least one genetic abnormality selected from NPM1 gene mutation, DNMT3A gene mutation, FLT gene mutation, and MLL translocation.

(Item A46)

The use of any one of Items A1 to A44, wherein the medicament is administered to a subject having at least one genetic abnormality selected from NPM1 gene mutation and MLL translocation.

(Item A47)

The use of any one of Items A1 to A44, wherein the medicament is administered to a subject having NPM1 gene mutation.

(Item A48)

The use of Item A47, wherein the subject having NPM1 gene mutation is determined based on (1) a step of detecting the NPM1 gene mutation in cancer cells obtained from the subject, and (2) a step of determining presence/absence of the NPM1 gene mutation detected in step (1).

(Item A49)

The use of any one of Items A1 to A44, wherein the medicament is administered to a subject having MLL translocation.

(Item A50)

The use of Item A49, wherein the subject having MLL translocation is determined based on (1) a step of detecting the MLL translocation in cancer cells obtained from the subject, and (2) a step of determining presence/absence of the MLL translocation detected in step (1).

(Item A51)

The use of any one of Items A1 to A44, wherein the medicament is administered to a subject having FLT gene mutation.

(Item A52)

The use of Item A51, wherein the subject having FLT gene mutation is determined based on (1) a step of detecting the FLT gene mutation in cancer cells obtained from the subject, and (2) a step of determining presence/absence of the FLT gene mutation detected in step (1).

(Item A53)

The use of any one of Items A1 to A44, wherein the medicament is administered to a subject having DNMT3A gene mutation.

(Item A54)

The use of Item A53, wherein the subject having DNMT3A gene mutation is determined based on (1) a step of detecting the DNMT3A gene mutation in cancer cells obtained from the subject, and (2) a step of determining presence/absence of the DNMT3A gene mutation detected in step (1).

Furthermore, the present invention is described as follows:

(Item B1)

A method for treating or preventing a cancer, comprising orally administrating a therapeutically effective amount of 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide (hereinafter, it may be referred to as "free form") or a pharmaceutically acceptable salt thereof, or a hydrate or solvate thereof as an active ingredient to a subject in need thereof.

(Item B2)

The method of Item B1, wherein the active ingredient is administered once a day.

(Item B3)

The method of Item B1, wherein the active ingredient is administered twice a day.

(Item B4)

The method of any one of Items B1 to B3, wherein one dose of the active ingredient is 40 mg converted to the free form.

(Item B5)

The method of any one of Items B1 to B3, wherein one dose of the active ingredient is 60 mg converted to the free form.

(Item B6)

The method of any one of Items B1 to B3, wherein one dose of the active ingredient is 80 mg converted to the free form.

(Item B7)

The method of any one of Items B1 to B3, wherein one dose of the active ingredient is 100 mg converted to the free form.

(Item B8)

The method of any one of Items B1 to B3, wherein one dose of the active ingredient is 120 mg converted to the free form.

(Item B9)

The method of any one of Items B1 to B3, wherein one dose of the active ingredient is 140 mg converted to the free form.

(Item B10)

The method of any one of Items B1 to B3, wherein one dose of the active ingredient is 180 mg converted to the free form.

(Item B11)

The method of any one of Items B1 to B3, wherein one dose of the active ingredient is 200 mg converted to the free form.

(Item B12)

The method of any one of Items B1 to B3, wherein one dose of the active ingredient is 220 mg converted to the free form.

(Item B13)

The method of any one of Items B1 to B3, wherein one dose of the active ingredient is 240 mg converted to the free form.

(Item B14)

The method of any one of Items B1 to B3, wherein one dose of the active ingredient is 260 mg converted to the free form.

(Item B15)

The method of any one of Items B1 to B3, wherein one dose of the active ingredient is 280 mg converted to the free form.

(Item B16)

The method of any one of Items B1 to B3, wherein one dose of the active ingredient is 300 mg converted to the free form.

(Item B17)

The method of any one of Items B1 to B3, wherein one dose of the active ingredient is 320 mg converted to the free form.

(Item B18)

The method of any one of Items B1 to B3, wherein one dose of the active ingredient is 340 mg converted to the free form.

(Item B19)

The method of any one of Items B1 to B3, wherein one dose of the active ingredient is 360 mg converted to the free form.

(Item B20)

The method of any one of Items B1 to B3, wherein one dose of the active ingredient is 380 mg converted to the free form.

(Item B21)

The method of any one of Items B1 to B3, wherein one dose of the active ingredient is 400 mg converted to the free form.

(Item B22)

The method of any one of Items B1 to B3, wherein one dose of the active ingredient is 500 mg converted to the free form.

(Item B23)

The method of any one of Items B1 to B3, wherein one dose of the active ingredient is 600 mg converted to the free form.

(Item B24)

The method of any one of Items B1 to B23, wherein the active ingredient is administered in combination with a different drug or a pharmaceutically acceptable salt thereof, wherein the different drug is at least one drug selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(Item B25)

The method of any one of Items B1 to B23, wherein the active ingredient is administered in combination with a different drug or a pharmaceutically acceptable salt thereof, wherein the different drug is at least one drug selected from (1) venetoclax and azacitidine (2) cytarabine and daunorubicin, and (3) gilteritinib.

(Item B26)

The method of any one of Items B1 to B23, wherein the active ingredient is administered in combination with gilteritinib once a day.

(Item B27)

The method of any one of Items B1 to B23, wherein the active ingredient is administered in combination with 120 mg of gilteritinib.

(Item B28)

The method of any one of Items B1 to B27, wherein the cancer is leukemia, polycythemia vera, malignant lymphoma, B-cell lymphoma, myeloma, brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item B29)

The method of any one of Items B1 to B27, wherein the cancer is leukemia, B-cell lymphoma, neuroblastoma, or prostate cancer.

(Item B30)

The method of any one of Items B1 to B27, wherein the cancer is leukemia.

(Item B31)

The method of any one of Items B28 to B30, wherein the leukemia is acute leukemia, chronic lymphocytic leukemia, or chronic myeloid leukemia.

(Item B32)

The method of Item B31, wherein the acute leukemia is MLL acute leukemia, MLL partial tandem duplicate acute leukemia, or NPM1 mutated acute leukemia.

(Item B33)

The method of Item B31, wherein the acute leukemia is MLL acute leukemia or NPM1 mutated acute leukemia.

(Item B34)

The method of Item B31, wherein the acute leukemia is acute myeloid leukemia with MLL rearrangement.

(Item B35)

The method of Item B31, wherein the acute leukemia is relapsed or refractory acute myeloid leukemia with MLL rearrangement.

(Item B36)

The method of Item B31, wherein the acute leukemia is acute lymphoid leukemia with MLL rearrangement.

(Item B37)

The method of Item B31, wherein the acute leukemia is relapsed or refractory acute lymphoid leukemia with MLL rearrangement.

(Item B38)

The method of Item B31, wherein the acute leukemia is acute myeloid leukemia with NPM1 mutation.

(Item B39)

The method of Item B31, wherein the acute leukemia is relapsed or refractory acute myeloid leukemia with NPM1 mutation.

(Item B40)

The method of Item B31, wherein the acute leukemia is leukemia accompanied by high expression of HOXa gene cluster or MEIS gene cluster.

(Item B41)

The method of any one of Items B1 to B27, wherein the cancer is tumor accompanied by p53 gain-of-function mutation.

(Item B42)

The method of any one of Items B1 to B27, wherein the cancer exhibits at least one genetic abnormality selected from NPM1 gene mutation, DNMT3A gene mutation, FLT gene mutation, and MLL translocation.

(Item B43)

The method of any one of Items B1 to B27, wherein the cancer exhibits at least one genetic abnormality selected from NPM1 gene mutation, FLT gene mutation, and MLL translocation.

(Item B44)

The method of any one of Items B1 to B27, wherein the cancer exhibits at least one genetic abnormality selected from NPM1 gene mutation and MLL translocation.

(Item B45)

The method of any one of Items B1 to B44, wherein the subject in need thereof has at least one genetic abnormality selected from NPM1 gene mutation, DNMT3A gene mutation, FLT gene mutation, and MLL translocation.

(Item B46)

The method of any one of Items B1 to B44, wherein the subject in need thereof has at least one genetic abnormality selected from NPM1 gene mutation and MLL translocation.

(Item B47)

The method of any one of Items B1 to B44, wherein the subject in need thereof has NPM1 gene mutation.

(Item B48)

The method of Item B47, wherein the subject having NPM1 gene mutation is determined based on (1) a step of detecting the NPM1 gene mutation in cancer cells obtained from the subject, and (2) a step of determining presence/absence of the NPM1 gene mutation detected in step (1).

(Item B49)

The method of any one of Items B1 to B44, wherein the subject in need thereof has MLL translocation.

(Item B50)

The method of Item B49, wherein the subject having MLL translocation is determined based on (1) a step of detecting the MLL translocation in cancer cells obtained from the subject, and (2) a step of determining presence/absence of the MLL translocation detected in step (1).

(Item B51)

The method of any one of Items B1 to B44, wherein the subject in need thereof has FLT gene mutation.

(Item B52)

The method of Item B51, wherein the subject having FLT gene mutation is determined based on (1) a step of detecting the FLT gene mutation in cancer cells obtained from the subject, and (2) a step of determining presence/absence of the FLT gene mutation detected in step (1).

(Item B53)

The method of any one of Items B1 to B44, wherein the subject in need thereof has DNMT3A gene mutation.

(Item B54)

The method of Item B53, wherein the subject having DNMT3A gene mutation is determined based on (1) a step of detecting the DNMT3A gene mutation in cancer cells obtained from the subject, and (2) a step of determining presence/absence of the DNMT3A gene mutation detected in step (1).

Effect of Invention

The technology of the present disclosure is useful as a medicament for treating and/or preventing leukemia, polycythemia vera, malignant lymphoma, B-cell lymphoma, myeloma, brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer, by using the compound disclosed herein in the usage and dosage as provided herein, and said medicament exhibits excellent anticancer effects against a cancer having a specific gene mutation. The technology of the present disclosure can be used as a variety of therapeutic and/or prophylactic agents by administering to humans at doses confirmed or expected to be tolerable, but should not be limited thereto. Furthermore, the anticancer effect can be further enhanced by using the present compound and a combination drug.

The purpose of the present invention is to provide an invention related to the usage and dosage of an optically active azabicyclo ring derivative that exerts excellent anticancer effects by inhibiting the binding between menin and a MLL fusion protein, and to provide a useful therapeutic drug and method for treating tumors having a specific gene mutation in combination with another anticancer agent.

In more detail, the present inventors provide technology related to a medicament comprising 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide, or a pharmaceutically acceptable salt thereof, or a hydrate or solvate thereof (hereinafter, it may be referred to as "the present compound").

DESCRIPTION OF EMBODIMENTS

Figure 1:
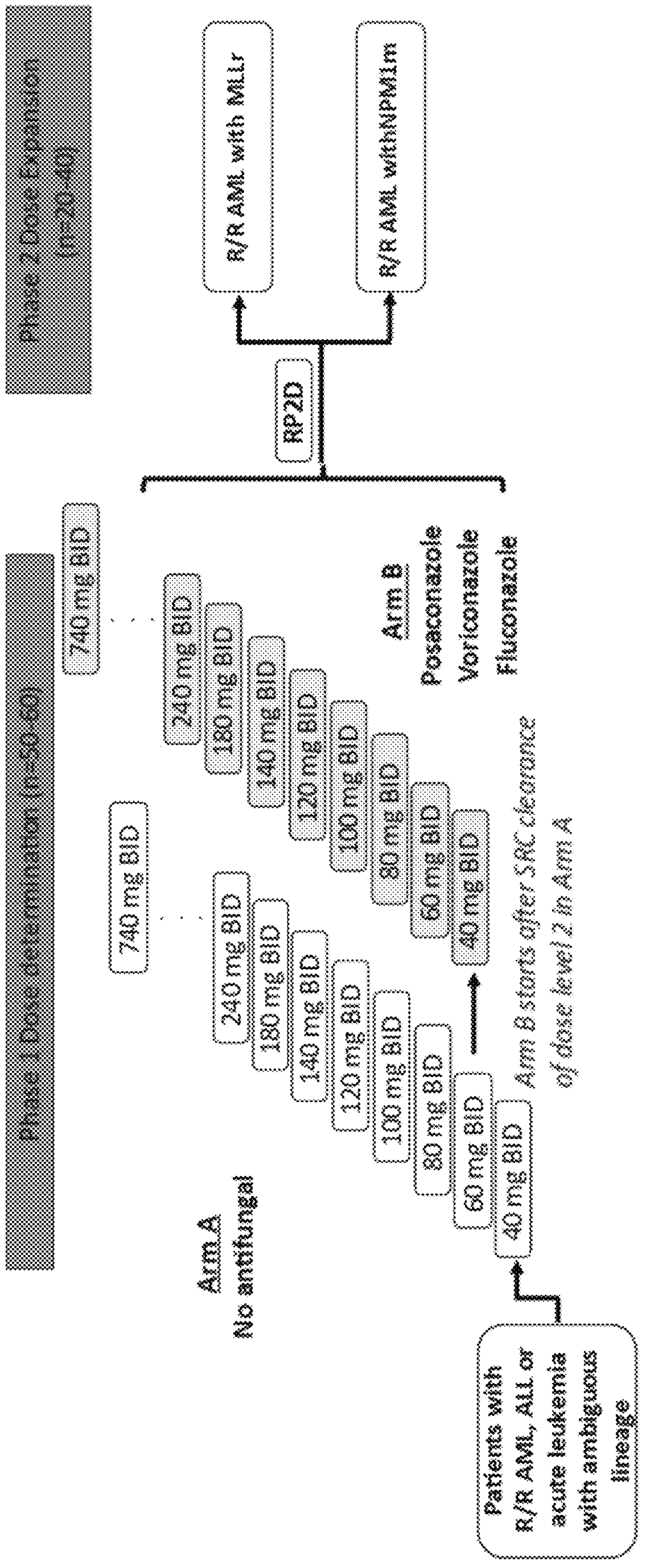
FIG. 1 shows the test design of the clinical test with the present compound, wherein the clinical test is a first-in-human (FIH) study, a Phase 1/2 study, consisting of a Phase 1 dose escalation part and a Phase 2 dose expansion part.

It should be understood that throughout the present specification, expressions in the singular also include the concept of the plural, unless otherwise indicated. Accordingly, articles in the singular (e.g. "a", "an", "the", etc. in the English language) should be understood to include their plural forms as well, unless otherwise indicated. Also, it should be understood that the terms used in the present specification have the meanings commonly used in the relevant field, unless otherwise indicated. Thus, unless otherwise defined, all technical and scientific terms used herein have the same meaning as commonly understood by a skilled person in the art to which the present disclosure belongs. In case of conflict, the present specification (including definitions) will control. 5-Fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl)oxy]-N,N-di (propan-2-yl)benzamide (free form of the present compound) has the following structure.

[Chem. 1]

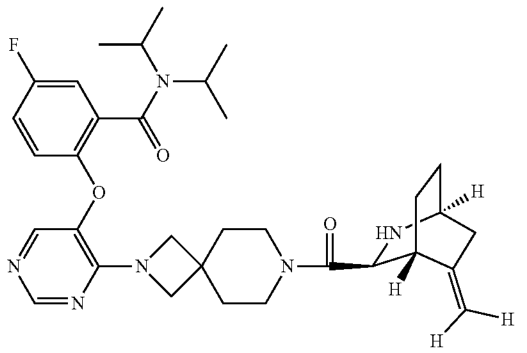

In addition, the "hydrate or solvate" in "free form of the present compound or a pharmaceutically acceptable salt thereof, or a hydrate or solvate thereof" includes a hydrate or solvate of the free from of the present compound, and a hydrate or solvate of a pharmaceutically acceptable salt of the present compound.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

"Tartrate of the present compound" means 5-fluoro-2-[(4-{7-[(1S,3S,4R)-5-methylidene-2-azabicyclo[2.2.2]octane-3-carbonyl]-2,7-diazaspiro[3.5]nonan-2-yl}pyrimidin-5-yl) oxy]-N,N-di(propan-2-yl)benzamide 1L(+)-tartrate.

The compound provided herein can encompass a variety of stereochemical forms. The compound of the present invention encompasses not only optical isomers but also diastereomers, which includes a for example, a mixture of enantiomers racemic mixture, and individual enantiomers and diastereomers that result from structural asymmetry in a particular compound. Separation of individual isomers or selective synthesis of individual isomers is achieved by applying various methods known to those skilled in the art.

The present compound also includes various hydrates, solvates, and crystal polymorphs. Furthermore, the compound of the present invention is substituted with an isotopic element (e.g., $^{2}H$ (or D), $^{3}H$ (or T), $^{11}C$, $^{13}C$, $^{14}C$, $^{13}N$, $^{15}N$, $^{15}O$, $^{35}S$, $^{18}F$, $^{125}I$, etc.). These compounds are also included in the compound of the present invention.

In addition, the scope disclosed herein includes a prodrug of the present compound. In the present disclosure, a prodrug refers to a derivative that is decomposed in vivo by acid hydrolysis or enzymatically to yield the present compound. For example, a prodrug can be produced by modifying the amino group of the present compound according to a conventional method. Specifically, it includes a compound in which the amino group is substituted with an alkanoyl group to become an alkanoylamino group, a compound in which the amino group is substituted with an alkoxycarbonyl group to become an alkoxycarbonylamino group, a compound in which the amino group is transformed to an alkanoyloxymethylamino group, and a compound in which the amino group is transformed to a hydroxylamine.

Hereinafter, terms used herein are explained as follows.

In some embodiments, the subject treated by the above methods is a mammal. The present compound can be used to mammals, and the term "mammal" is used herein in its normal biological meaning. Accordingly, it includes, for example, humans, cows, horses, dogs, cats, rats, mice, but also many other species. In some further embodiments, the subject is a human.

If it is desirable to fix the compound of the present invention as a pharmaceutically acceptable salt, when the present compound is obtained as a pharmaceutically acceptable salt, it may be purified without further reaction, and when it is obtained in a free form, it may be dissolved or suspended in an appropriate organic solvent and an acid or base may be added therein to form a salt in a general manner.

In the present invention, the "drug used in combination" or "combination drug" is an antitumor medicament which can be used in combination with the compound of the present invention or can be combined with the compound of the present invention in a pharmaceutical composition. The "drug used in combination" includes, for example, an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an immune checkpoint inhibitor, an epigenetics-associated molecular inhibitor, a protein post-translational modification inhibitor, and other antitumor medicaments. Examples of the "drug used in combination" include, for example, azacitidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, Gemtuzumab ozogamicin, inotuzumab ozogamicin, venetoclax, gilteritinib, and the like.

The antitumor tyrosine kinase inhibitor includes, for example, an FLT3 inhibitor. The FLT3 inhibitor includes, for example, gilteritinib, quizartinib, midostaurin. The FLT3 inhibitor includes, preferably, gilteritinib.

It is desirable that gilteritinib is orally administered once a day, and one dose of the active ingredient includes, preferably 80 mg and 120 mg which are converted to the free form, more preferably 120 mg which is converted to the free form.

In case that the present compound is used in combination with once-daily 120 mg of gilteritinib (converted to the free form), it is desirable that the medicament comprising the present compound or a pharmaceutically acceptable salt thereof, or a hydrate or solvate thereof is orally administered twice a day, and one dose of the active ingredient includes, preferably 140 mg, 200 mg, and 300 mg which are converted to the free form of the present compound.

In case that the present compound is used in combination with once-daily 80 mg of gilteritinib (converted to the free form), it is desirable that the medicament comprising the present compound or a pharmaceutically acceptable salt thereof, or a hydrate or solvate thereof is orally administered twice a day, and one dose of the active ingredient includes, preferably 100 mg, 120 mg, and 140 mg which are converted to the free form of the present compound.

The combination drug used herein includes, for example, a BCL-2 inhibitor. The BCL-2 inhibitor includes, for example, venetoclax.

It is desirable that venetoclax is orally administered once a day, and one dose of the active ingredient includes, preferably 100 mg, 200 mg, and 400 mg which are converted to the free form.

For venetoclax 100 mg dosing, venetoclax dosing begins with a 4-day ramp-up with 10 mg on Day 1, 20 mg on Day 2, 50 mg on Day 3, and 100 mg on Day 4, followed by 100 mg daily on Days 5-14 of each 28-day cycle. For venetoclax 200 mg dosing, a 4-day ramp-up begins with 20 mg on Day 1, 50 mg on Day 2, 100 mg on Day 3, and 200 mg on Day 4, followed by 200 mg daily on Days 5-14 of each 28-day cycle. For venetoclax 400 mg dosing, a 3-day ramp-up begins with 100 mg on Day 1, 200 mg on Day 2, 400 mg on Day 3, followed by 400 mg daily on Days 4-14 of each 28-day cycle.

The epigenetics-associated molecular inhibitor includes, for example, azacitidine.

It is desirable that azacitidine is intravenously administered once a day, and one dose of the active ingredient includes, preferably 75 mg/$m^2$ which is converted to the free form.

Azacitidine 75 mg/$m^2$ is administered intravenously or subcutaneously once daily on Days 1-7 of each 28-day cycle.

In case that the present compound is used in combination with once-daily 100 mg of venetoclax (converted to the free form) and once-daily azacitidine 75 mg/$m^2$ (converted to the free form), it is desirable that the medicament comprising the present compound or a pharmaceutically acceptable salt thereof, or a hydrate or solvate thereof is orally administered twice a day, and one dose of the active ingredient includes, preferably 140 mg, 200 mg, and 300 mg which are converted to the free form of the present compound.

In case that the present compound is used in combination with once-daily 200 mg of venetoclax (converted to the free form) and once-daily azacitidine 75 mg/$m^2$ (converted to the free form), it is desirable that the medicament comprising the present compound or a pharmaceutically acceptable salt thereof, or a hydrate or solvate thereof is orally administered twice a day, and one dose of the active ingredient includes, preferably 140 mg, 200 mg, and 300 mg which are converted to the free form of the present compound.

In case that the present compound is used in combination with once-daily 400 mg of venetoclax (converted to the free form) and once-daily azacitidine 75 mg/$m^2$ (converted to the free form), it is desirable that the medicament comprising the present compound or a pharmaceutically acceptable salt thereof, or a hydrate or solvate thereof is orally administered twice a day, and one dose of the active ingredient includes, preferably 140 mg, 200 mg, and 300 mg which are converted to the free form of the present compound.

The administration interval of the present compound and the combination drug herein should not be limited, and they may be administered to a subject at the same time or with a time difference. Or, the present compound and the combination drug may be also used as a combined formulation. The dosage of the combination drug can be appropriately selected based on the clinically used dosage. And, the combination ratio of the present compound and the combination drug can be appropriately selected depending on the subject for administration, administration route, target disease, symptoms, combination, etc.

"MOLM-13 cells" are a human acute myeloid leukemia cell line that has MLL-AF9 fusion protein and FLT3-ITD mutation. "OCI-AML3 cells" are a human acute myeloid leukemia cell line that has NPM1 mutation and DNMT3A mutation.

The frequency of oral administration of the medicament comprising the present compound or a pharmaceutically acceptable salt thereof, or a hydrate or solvate thereof includes once a day, twice a day, three times a day, and four times a day, preferably once a day or twice a day, more preferably twice a day.

The "XXX mg converted to the free form" means that one dose of the active ingredient is administered that equals the moles of the free form of the indicated weight (XXX mg). For example, the dose of tartrate of the present compound is calculated using the following formula.

[Dose of tartrate of the present compound]=[dose of the present compound (free form)]×[molecular weight (740.83) of tartrate of the present compound]/[molecular weight (590.74) of the present compound (free form)]

For example, the "20 mg converted to the free form" corresponds to 25 mg of tartrate of the present compound, which is calculated using the following formula.

[Dose of tartrate of the present compound]=20 mg×[molecular weight (740.83) of tartrate of the present compound]/[molecular weight (590.74) of the present compound (free form)]=25 mg Similar calculations can be made for other forms of salts, hydrates, solvates, etc.

One oral dose of the present compound or a pharmaceutically acceptable salt thereof, or a hydrate or solvate thereof in the medicament includes 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, 1010 mg, 1020 mg, 1030 mg, 1040 mg, 1050 mg, 1060 mg, 1070 mg, 1080 mg, 1090 mg, 1100 mg, 1110 mg, 1120 mg, 1130 mg, 1140 mg, 1150 mg, 1160 mg, 1170 mg, 1180 mg, 1190 mg, and 1200 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, preferably, 20 mg, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, 600 mg, 620 mg, 630 mg, 640 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, 1010 mg, 1020 mg, 1030 mg, 1040 mg, 1050 mg, 1060 mg, 1070 mg, 1080 mg, 1090 mg, 1100 mg, 1110 mg, 1120 mg, 1130 mg, 1140 mg, 1150 mg, 1160 mg, 1170 mg, 1180 mg, 1190 mg, and 1200 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, more preferably, 20 mg, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, 600 mg, 620 mg, 630 mg, 640 mg, 670 mg, 680 mg, 690 mg, 700 mg, 710 mg, 720 mg, 730 mg, and 740 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, even more preferably, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, and 600 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, the most preferably, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, and 500 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, in another preferred embodiment, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, and 400 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, in another preferred embodiment, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, and 500 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, in another more preferred embodiment, 300 mg, 320 mg, 340 mg, 360 mg, 380 mg, 400 mg, 420 mg, 440 mg, 460 mg, 480 mg, and 500 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, in another more preferred embodiment, 360 mg, 380 mg, 400 mg, 420 mg, and 440 mg which are converted to the free form of the present compound. And, it also includes the range between these two arbitrarily-selected doses.

One oral dose of the present compound or a pharmaceutically acceptable salt thereof, or a hydrate or solvate thereof in the medicament includes, in another most preferred embodiment, 300 mg which is converted to the free form of the present compound.

One oral dose of the present compound or a pharmaceutically acceptable salt thereof, or a hydrate or solvate thereof in the medicament includes, in another most preferred embodiment, 400 mg which is converted to the free form of the present compound.

It is desirable that the medicament comprising the present compound or a pharmaceutically acceptable salt thereof, or a hydrate or solvate thereof is orally administered twice a day, and one dose of the active ingredient includes, preferably, 40 mg, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, and 600 mg which are converted to the free form of the present compound. And, the one dose also includes the range between these two arbitrarily-selected doses.

It is desirable that the medicament comprising the present compound or a pharmaceutically acceptable salt thereof, or a hydrate or solvate thereof is orally administered twice a day, and one dose of the active ingredient includes, preferably, 60 mg, 80 mg, 100 mg, 120 mg, 140 mg, 160 mg, 180 mg, 200 mg, 220 mg, 240 mg, 260 mg, 280 mg, 300 mg, 320 mg, 340 mg, 360 mg, 380 mg, and 400 mg which are converted to the free form of the present compound. And, the one dose also includes the range between these two arbitrarily-selected doses.

It is desirable that the medicament comprising the present compound or a pharmaceutically acceptable salt thereof, or a hydrate or solvate thereof is orally administered twice a day, and one dose of the active ingredient includes, more preferably, 200 mg, 220 mg, 240 mg, 260 mg, 280 mg, 300 mg, 320 mg, 340 mg, 360 mg, 380 mg, 400 mg, 420 mg, 440 mg, 460 mg, 480 mg, and 500 mg which are converted to the free form of the present compound. And, the one dose also includes the range between these two arbitrarily-selected doses.

It is desirable that the medicament comprising the present compound or a pharmaceutically acceptable salt thereof, or a hydrate or solvate thereof is orally administered twice a day, and one dose of the active ingredient includes, the most preferably, 300 mg, 320 mg, 340 mg, 360 mg, 380 mg, 400 mg, 420 mg, 440 mg, 460 mg, 480 mg, and 500 mg which are converted to the free form of the present compound. And, the one dose also includes the range between these two arbitrarily-selected doses.

It is desirable that the medicament comprising the present compound or a pharmaceutically acceptable salt thereof, or a hydrate or solvate thereof is orally administered twice a day, and one dose of the active ingredient includes, in another preferred embodiment, 360 mg, 380 mg, 400 mg, 420 mg, and 440 mg which are converted to the free form of the present compound. And, the one dose also includes the range between these two arbitrarily-selected doses.

It is desirable that the medicament comprising the present compound or a pharmaceutically acceptable salt thereof, or a hydrate or solvate thereof is orally administered twice a day, and one dose of the active ingredient includes, in another more preferred embodiment, 300 mg which is converted to the free form of the present compound.

It is desirable that the medicament comprising the present compound or a pharmaceutically acceptable salt thereof, or a hydrate or solvate thereof is orally administered twice a day, and one dose of the active ingredient includes, in another more preferred embodiment, 400 mg which is converted to the free form of the present compound.

The present compound or a pharmaceutically acceptable salt thereof, or a hydrate or solvate thereof can be orally administrated directly or as a suitable drug formulation. The dosage form includes, for example, a tablet, a capsule, a powder, a granule, a liquid, a suspension, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, lactose hydrate, mannitol, D-mannitol, crystalline cellulose, low-substituted hydroxypropylcellulose, corn starch, sodium starch glycolate, partially-pregelatinized starch, carmellose, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, light silicic anhydride, talc, and the like.

As one embodiment of the above drug formulation, Formulation A comprising the ingredients shown below may be exemplified.

(i) tartrate of the present compound
(ii) D-mannitol
(iii) partially-pregelatinized starch
(iv) croscarmellose sodium
(v) hydroxypropylcellulose, and
(vi) sodium stearyl fumarate.

As one embodiment of the above drug formulation, Formulation B comprising the ingredients shown below may be exemplified.

(i) tartrate of the present compound
(ii) lactose hydrate
(iii) crystalline cellulose
(iv) carmellose
(v) light silicic anhydride, and
(vi) sodium stearyl fumarate.

Formulation A or Formulation B described above can be used in the following examples.

EXAMPLES

The present invention is explained in more detail in the following by referring to Examples; however, the technical scope of the present invention should not be limited thereto. In the examples below, tartrate salt of the present compound is used as an active ingredient, and all the doses (mg) indicated in (1) Study Design Considerations, (2) Patient Enrollment, and Examples 1-13 are doses (mg) converted to the free form. For example, "20 mg" means 20 mg of the present compound (free form), and the weight of the tartrate of the present compound used in this case is 25 mg.

(1) Study Design Considerations

The present clinical test using the present compound is a Phase 1/2 FIH study which includes a Phase 1 dose escalation part and a Phase 2 dose expansion part. The study design of the present clinical test is summarized in FIG. 1. Originally, the planned provisional dose level included only 40, 60, 80, 100, 120, and 140 mg BID, but the additional planned provisional dose levels (180, 240, 320, 420, 560, 740 mg BID) were included in the present test because there is no safety issue thus far.

In the dose-escalation part, patients were assigned to separate study arms, based on their concomitant treatment with or without azole antifungals, a strong or moderate CYP3A4/5 inhibitor, as follows:

Arm A: Patients without azole antifungal treatment within 7 days (or 21 days for isavuconazole) of first dose of the present compound Arm B: Patients receiving posaconazole, voriconazole, or fluconazole antifungal prophylaxis at enrollment The safety of each dose level also was evaluated by the SRC, which was comprised of all investigators participating in the study and selected Sponsor study team members. The dose recommended by the BLRM method was treated as guidance and was integrated with a clinical assessment of toxicity information and review of other available data, including safety, PK, pharmacodynamic, and laboratory data.

(2) Patient Enrollment

At the data cut-off date, a total of 14 patients have been enrolled in the Phase 1 dose escalation part of the present study at dose levels of 40 mg BID (N=2), 80 mg BID (N=4), 100 mg BID (N=2), and 120 mg BID (N=6) in Arm A. A total of 10 patients have been enrolled at dose levels of 40 mg BID (N=4) and 60 mg BID (N=6) in Arm B (Table 1).

When the Dose Limiting Toxicity (DLT) evaluation for each cohort was completed, the SRC determined a next dose level based on the DLT and other available data, including safety, PK, pharmacodynamic, and laboratory data with reference to the Bayesian Logistic Regression Model (BLRM) recommendation.

When the Safety Review Committee (SRC) determined 80 mg BID in Arm A is safe after 2 patients were evaluated in the cohort, SRC decided to open Arm B from 40 mg BID. Importantly, as of the opening of Arm B, enrollment into the study has been limited to patients with specific genetic abnormalities in both Arm A and Arm B. Therefore, the SRC determined to continue with 80 mg BID in Arm A and open 40 mg BID in Arm B for patients with specific gene abnormalities. These genetic mutations are those where data has shown that the present compound may be of benefit, such as MLLr or NPM1m. By narrowing the population to patients who are more likely to respond to the present compound, a more accurate assessment of potential toxicity in the target population can be determined.

Dose escalation decisions were made after all patients in a dose level cohort have at least completed Cycle 1. All available data were presented along with the BLRM predictions for toxicity probabilities at the potential next dose levels. The SRC then determined the dose(s) for the next cohort(s).

TABLE 1

| Dose (mg BID)/Arm | All patient N |
|---|---|
| 40/A (all comer) | 2 |
| 80/A (all comer and selected population*) | 4 (2 all comer, 2 selected population) |
| 100/A (selected population) | 2 |
| 120/A (selected population) | 6 |
| 40/B* (selected population) | 4 |
| 60/B (selected population) | 6 |

*As of the opening of Arm B, which is the same timing when the SRC determined to continue 80 mg BID in Arm A after 2 patients evaluated in the cohort, enrollment into the study has been limited to patients with specific genetic anomalies.

Example 1: Safety Evaluation of the Present Compound

At the time of data cutoff, none of 24 patients enrolled in the present clinical test developed DLT (Table 2). All the 24 patients experienced at least one treatment-emergent adverse event (TEAE) while receiving the test drug. The number of patients who developed Grade 3 or Grade 4 TEAEs was about the same level between the Arms A and B, i.e., 5 (35.7%) patients and 4 (28.6%) patients in Arm A, and 3 (30.0%) patients and 2 (20.0%) patients in Arm B. Three patients in Arm B had treatment related grade 3 TEAEs (Aspartate aminotransferase increased, leukocytosis, and hypertriglyceridemia) and all of them were transient and recovered/resolved. Serious TEAEs were reported in 9 (64.3%) patients in Arm A and 6 (60.0%) patients in Arm B. Only one serious TEAE (2 occurrences of differentiation syndrome in one patient in Arm A) was judged to be treatment-related by the Investigator. Details regarding serious TEAEs are provided in Table 6. Five (35.7%) patients in Arm A and 3 (30.0%) patients in Arm B died during the study due to TEAEs, but none of them were judged to be treatment-related. Furthermore, 2 out of 5 patients in Arm A and 2 out of 3 patients in Arm B died due to the progression of disease under study (refer Table 5). There was 1 patient in Arm A and 2 patients in Arm B with TEAE related to the present compound that led to dose interruption. No related TEAE leading to dose withdrawn or dose reduction has been reported thus far.

The adverse events (AEs) observed to date have been consistent with AEs observed in patients who have relapsed/refractory AML with other treatment such as anemia, hypokalemia, nausea, fatigue, and headache etc. AE profile was generally consistent between Arm A and Arm B. The majority of TEAEs related to the present compound were Grade 1 or 2. Refer to Table 4 for a tabulation of TEAEs in ≥20% of patients at least in either Arm A or Arm B regardless of causality, and Table 4 for a tabulation of all TEAEs related to the present compound.

As shown in Table 2 and Table 5, serious adverse events (SAEs) were reported in 15 patients total: 9 (64.3%) patients in Arm A and 6 (60.0%) patients in Arm B. These SAEs were consistent with complications common in patients with AML and were all assessed as not related to the present compound, except for 2 SAEs of differentiation syndrome in 1 patient, which were both assessed by the Investigator as related to the present compound.

The patient who experienced potential differentiation syndrome was a 63-year-old female with AML characterized by a TP53 mutation. She was enrolled in Arm A and received 80 mg BID. The diagnosis of possible differentiation syndrome was based on the observation of increasing WBC count with decreases in the percent of blasts associated with the present compound administration near the end of Cycle 1 and beginning of Cycle 2. The assessment, however, was complicated by AML progression (bone marrow blasts increasing from 11% at baseline to 53% on Cycle 1 Day 28), transfusion reaction, and pneumonia of potential fungal etiology. The SAE of differentiation syndrome resolved, however, the patient died of an intracranial hemorrhage secondary to progression of AML shortly thereafter; platelet count was 20,000/μL at the day before the occurrence of an intracranial hemorrhage, which indicates the progression of AML. The investigator noted that the finding of possible differentiation syndrome did not contribute to the patient's death. No other cases of differentiation syndrome have been observed to date and no cases of differentiation syndrome have occurred in patients with MLLr or NPM1m.

Fatal SAEs occurred in 8 patients (5 patients in Arm A and 3 patients in Arm B), and all were assessed by the Investigator and the Sponsor as unrelated to the present compound, and most likely secondary to AML progression or complications associated with AML.

Overall, the types and frequencies of TEAEs between Arm A and Arm B are similar. The only related SAE were differentiation syndrome in 1 patient in Arm A described above. Other SAEs, including fatal AEs, were consistent with complications associated with recurrent, progressive AML. No unique safety findings in Arm B patients have been observed to date and the safety profile of the present compound between Arm A and Arm B is not different.

TABLE 2

| | Dose (mg BID)/Arm (N) | | | | | | | |
|---|---|---|---|---|---|---|---|---|
| | 40/A (2) n (%) | 80/A (4) n (%) | 100/A (2) n (%) | 120/A (6) n (%) | All/A (14) n (%) | 40/B (4) n (%) | 60/B (6) n (%) | All/B (10) n (%) |
| Patients with any DLTs | 0 (0.0) | 0 (0.0) | 0 (0.0) | 0 (0.0) | 0 (0.0) | 0* (0.0) | 0 (0.0) | 0 (0.0) |
| Patients with any TEAEs | 2 (100.0) | 4 (100.0) | 2 (100.0) | 6 (100.0) | 14 (100.0) | 4 (100.0) | 6 (100.0) | 10 (100.0) |
| Patients with at least 1 Grade 3 TEAE as maximum toxicity grade | 1 (50.0) | 1 (25.0) | 0 (0.0) | 3 (50.0) | 5 (35.7) | 2 (50.0) | 1 (16.7) | 3 (30.0) |
| Patients with at least 1 Grade 4 TEAE as maximum toxicity grade | 1 (50.0) | 0 (0.0) | 1 (50.0) | 2 (33.3) | 4 (28.6) | 0 (0.0) | 2 (33.3) | 2 (20.0) |
| Patients with at least one SAE | 1 (50.0) | 3 (75.0) | 2 (100.0) | 3 (50.0) | 9 (64.3) | 4 (100.0) | 2 (33.3) | 6 (60.0) |
| TEAEs leading to Death | 0 (0.0) | 3 (75.0) | 1 (50.0) | 1 (16.7) | 5 (35.7) | 2 (50.0) | 1 (16.7) | 3 (30.0) |
| Patients with TEAEs Leading to permanent discontinuation | 0 (0.0) | 1 (25.0) | 1 (50.0) | 1 (16.7) | 3 (21.4) | 0 (0.0) | 1 (16.7) | 1 (10.0) |
| Patients with TEAEs Leading to dose reduction | 0 (0.0) | 0 (0.0) | 0 (0.0) | 0 (0.0) | 0 (0.0) | 0 (0.0) | 0 (0.0) | 0 (0.0) |
| Patients with TEAEs Leading to drug interruption | 0 (0.0) | 2 (50.0) | 1 (50.0) | 0 (0.0) | 3 (21.4) | 3 (75.0) | 0 (0.0) | 3 (30.0) |
| Patients with any TEAEs related to the present compound | 0 (0.0) | 2 (50.0) | 2 (100.0) | 3 (50.0) | 7 (50.0) | 3 (75.0) | 1 (16.7) | 4 (40.0) |
| Patients with at least 1 related Grade 3 TEAE as maximum toxicity grade | 0 (0.0) | 0 (0.0) | 0 (0.0) | 0 (0.0) | 0 (0.0) | 2 (50.0) | 1 (16.7) | 3 (30.0) |
| Patients with at least 1 Grade 4 related TEAE as maximum toxicity grade | 0 (0.0) | 1 (25.0) | 0 (0.0) | 0 (0.0) | 1 (7.1) | 0 (0.0) | 0 (0.0) | 0 (0.0) |
| Patient with related TEAEs leading to Death | 0 (0.0) | 0 (0.0) | 0 (0.0) | 0 (0.0) | 0 (0.0) | 0 (0.0) | 0 (0.0) | 0 (0.0) |
| Patient with at least 1 related SAE | 0 (0.0) | 1 (25.0) | 0 (0.0) | 0 (0.0) | 1 (7.1) | 0 (0.0) | 0 (0.0) | 0 (0.0) |
| Patients with related TEAEs Leading to permanent discontinuation | 0 (0.0) | 0 (0.0) | 0 (0.0) | 0 (0.0) | 0 (0.0) | 0 (0.0) | 0 (0.0) | 0 (0.0) |
| Patients with related TEAEs Leading to dose reduction | 0 (0.0) | 0 (0.0) | 0 (0.0) | 0 (0.0) | 0 (0.0) | 0 (0.0) | 0 (0.0) | 0 (0.0) |
| Patients with related TEAEs Leading to drug interruption | 0 (0.0) | 1 (25.0) | 0 (0.0) | 0 (0.0) | 1 (7.1) | 2 (50.0) | 0 (0.0) | 2 (20.0) |

*One patient in 40 mg BID in Arm B was not DLT evaluable.

TABLE 3

| MedDRA System organ class/Preferred Term | Arm A*[1] N = 14 Any Grade n (%) | Arm A*[1] N = 14 ≥Grade 3 n (%) | Arm B*[2] N = 10 Any Grade n (%) | Arm B*[2] N = 10 ≥Grade 3 n (%) |
|---|---|---|---|---|
| Patients with Any TEAE | 14 (100.0) | 14 (100.0) | 10 (100.0) | 8 (80.0) |
| Blood and lymphatic system disorders | 10 (71.4) | 8 (57.1) | 3 (30.0) | 3 (30.0) |
| Anaemia | 5 (35.7) | 4 (28.6) | 1 (10.0) | 0 |
| Infections and Infestations | 8 (57.1) | 6 (42.9) | 6 (60.0) | 4 (40.0) |
| Pneumonia | 2 (14.3) | 2 (14.3) | 2 (20.0) | 2 (20.0) |
| Sepsis | 2 (14.3) | 2 (14.3) | 2 (20.0) | 2 (20.0) |
| Metabolism and nutrition disorders | 11 (78.6) | 1 (7.1) | 5 (50.0) | 4 (40.0) |
| Hypokalaemia | 2 (14.3) | 0 | 3 (30.0) | 3 (30.0)*[3] |
| Hypocalcaemia | 3 (21.4) | 0 | 1 (10.0) | 1 (10.0) |
| Hypertriglyceridaemia | 1 (7.1) | 0 | 2 (20.0) | 1 (10.0) |
| Hyponatraemia | 4 (28.6) | 0 | 0 | 0 |
| Decreased appetite | 3 (21.4) | 0 | 0 | 0 |
| Hypoalbuminaemia | 3 (21.4) | 0 | 0 | 0 |
| Hypomagnaesemia | 3 (21.4) | 0 | 0 | 0 |
| Investigations | 10 (71.4) | 4 (28.6) | 3 (30.0) | 1 (10.0) |
| Aspartate aminotransferase increased | 2 (14.3) | 1 (7.1) | 2 (20.0) | 1 (10.0) |
| Platelet count decreased | 3 (21.4) | 1 (7.1) | 0 | 0 |
| Alanine aminotransferase increased | 1 (7.1) | 0 | 2 (20.0) | 0 |
| Gastrointestinal disorders | 9 (64.3) | 1 (7.1) | 6 (60.0) | 0 |
| Nausea | 5 (35.7) | 0 | 3 (30.0) | 0 |
| Constipation | 3 (21.4) | 0 | 1 (10.0) | 0 |
| Vomiting | 3 (21.4) | 0 | 1 (10.0) | 0 |
| Stomatitis | 1 (7.1) | 0 | 2 (20.0) | 0 |
| Hemorrhoids | 0 | 0 | 2 (20.0) | 0 |
| General disorders and administration site disorders | 8 (57.1) | 2 (14.3) | 3 (30.0) | 2 (20.0) |
| Disease progression | 1 (7.1) | 1 (7.1) | 2 (20.0) | 2 (20.0) |
| Fatigue | 3 (21.4) | 0 | 2 (20.0) | 0 |
| Pyrexia | 3 (21.4) | 0 | 0 | 0 |
| Oedema peripheral | 2 (14.3) | 0 | 0 | 0 |
| Nervous System Disorders | 7 (50.0) | 2 (14.3) | 2 (20.0) | 0 |
| Headache | 5 (35.7) | 0 | 1 (20.0) | 0 |
| Respiratory, thoracic and mediastinal disorders | 6 (42.9) | 2 (14.3) | 3 (30.0) | 0 |
| Dyspnoea | 3 (21.4) | 1 (7.1) | 1 (10.0) | 0 |
| Epistaxis | 1 (7.1) | 0 | 2 (20.0) | 0 |
| Musculoskeletal and connective tissue disorders | 7 (50.0) | 0 | 2 (20.0) | 1 (10.0) |
| Pain in extremity | 3 (21.4) | 0 | 1 (10.0) | 0 |
| Skin and subcutaneous tissue disorders | 5 (35.7) | 0 | 1 (10.0) | 0 |
| Pruritus | 3 (21.4) | 0 | 0 | 0 |

*[1]Arm A includes 40, 80, 100, and 120 mg BID dose levels.

*[2]Arm B includes 40 and 60 mg BID dose levels.

*[3]Grade 3 Hypokalemia (not related to the present compound) was observed in three patients in Arm B; 1) One patient had chronic kidney disease as a complication and the patient had electrolyte abnormalities at baseline. 2) Grade 3 hypokalemia started before the first dose of the present compound in the second patient. 3) Grade3 hypokalemia started 10 days later than the last dose of the present compound in the third patient. Also, the patient had Grade 1 hypomagnesaemia and Grade 1 Diarrhoea as a complication.

TABLE 4

| MedDRA System organ class/Preferred Term | Arm A*[1] N = 14 Any Grade n (%) | Arm A*[1] N = 14 ≥Grade 3 n (%) | Arm B*[2] N = 10 Any Grade n (%) | Arm B*[2] N = 10 ≥Grade 3 n (%) |
|---|---|---|---|---|
| Blood and lymphatic system disorders | 0 | 0 | 1 (10.0) | 1 (10.0) |
| Leukocytosis | 0 | 0 | 1 (10.0) | 1 (10.0) |
| Metabolism and nutrition disorders | 4 (28.6) | 0 | 1 (10.0) | 1 (10.0) |
| Decreased appetite | 2 (14.3) | 0 | 0 | 0 |
| Hyperuricaemia | 1 (7.1) | 0 | 0 | 0 |
| Increased appetite | 1 (7.1) | 0 | 0 | 0 |
| Hypertriglyceridaemia | 0 | 0 | 1 (10.0) | 1 (10.0) |
| Gastrointestinal disorders | 2 (14.3) | 0 | 1 (10.0) | 0 |
| Nausea | 2 (14.3) | 0 | 1 (10.0) | 0 |
| Vomiting | 2 (14.3) | 0 | 1 (10.0) | 0 |
| General disorders and administration site conditions | 1 (7.1) | 0 | 0 | 0 |
| Thirst | 1 (7.1) | 0 | 0 | 0 |
| Neoplasms benign, malignant and unspecified (incl cysts and polyps) | 1 (7.1) | 1 (7.1) | 0 | 0 |
| Differentiation syndrome | 1 (7.1) | 1 (7.1) | 0 | 0 |
| Nervous system disorders | 1 (7.1) | 0 | 0 | 0 |
| Headache | 1 (7.1) | 0 | 0 | 0 |
| Investigations | 0 | 0 | 1 (10.0) | 1 (10.0) |
| Aspartate aminotransferase increased | 0 | 0 | 1 (10.0) | 1 (10.0) |

*[1]Arm A includes 40, 80, 100, and 120 mg BID dose levels.
*[2]Arm B includes 40 and 60 mg BID dose levels.

TABLE 5

| Patient ID | Arm (mg BID), Dose level | Preferred term | CTCAE Grade | Relationship to the present compound | Action taken for the present compound | Outcome |
|---|---|---|---|---|---|---|
| JP002A-0001 | 40/A | Sepsis | 3 | Not related | Dose not changed | Not recovered/ Not resolved |
| US053A-0001 | 80/A | Pneumonia | 3 | Not related | Drug interrupted | Recovered/ Resolved |
| US053A-0001 | 80/A | Atrial fibrillation | 3 | Not related | Not applicable | Recovered/ Resolved |
| US053A-0001 | 80/A | Differentiation syndrome | 3 | Related | Not applicable | Recovered/ Resolved |
| US053A-0001 | 80/A | Differentiation syndrome | 4 | Related | Drug interrupted | Recovered/ Resolved |
| US053A-0001 | 80/A | Respiratory failure | 4 | Not related | Not applicable | Recovered/ Resolved |
| US053A-0001 | 80/A | Haemorrhage intracranial | 5 | Not related | Not applicable | Fatal |
| US154A-0001 | 80/A | Disease progression | 5 | Not related | Drug interrupted | Fatal |
| US210A-0001 | 80/A | Rectal haemorrhage | 4 | Not related | Drug withdrawn | Recovered/ Resolved |
| US210A-0001 | 80/A | Pneumonia fungal | 5 | Not related | Not applicable | Fatal |
| US154A-0004 | 100/A | Leukocytosis | 4 | Not related | Dose not changed | Recovering/ Resolving |
| US154A-0004 | 100/A | Pyrexia | 1 | Not related | Dose not changed | Recovered/ Resolved |
| US154A-0004 | 100/A | Respiratory failure | 2 | Not related | Dose not changed | Recovered/ Resolved |
| US185A-0001 | 100/A | Electrocardiogram QT prolonged*[1] | 3 | Not related | Drug interrupted | Recovered/ Resolved |
| US185A-0001 | 100/A | Haemorrhage intracranial | 2 | Not related | Dose not changed | Not recovered/ |

TABLE 5-continued

| Patient ID | Arm (mg BID), Dose level | Preferred term | CTCAE Grade | Relationship to the present compound | Action taken for the present compound | Outcome |
|---|---|---|---|---|---|---|
| | | | | | | Not resolved |
| US185A-0001 | 100/A | Cerebrovascular accident | 4 | Not related | Drug withdrawn | Not recovered/ Not resolved |
| US185A-0001 | 100/A | Acute myeloid leukaemia | 5 | Not related | Not applicable | Fatal |
| US158A-0002 | 120/A | Leukocytosis | 1 | Not related | Dose not changed | Recovered/ Resolved |
| US185A-0006 | 120/A | Sepsis | 5 | Not related | Drug withdrawn | Fatal |
| US185A-0006 | 120/A | Lung infection (pneumonia) | 5 | Not related | Drug withdrawn | Fatal |
| US185A-0006 | 120/A | Multiple organ dys function syndrome | 5 | Not related | Drug withdrawn | Fatal |
| US210A-0002 | 120/A | Cellulitis | 3 | Not related | Dose not changed | Recovered/ Resolved |
| JP028A-0001 | 40/B | Pneumonia*2 | 4 | Not related | Dose not changed | Recovered/ Resolved |
| JP028A-0001 | 40/B | Pneumonia*2 | 5 | Not related | Dose not changed | Fatal |
| US053A-0002 | 40/B | COVID-19 | 3 | Not related | Not applicable | Recovered/ Resolved |
| US053A-0002 | 40/B | Pneumonia | 3 | Not related | Not applicable | Recovered/ Resolved |
| US154A-0002 | 40/B | Bone pain | 3 | Not related | Drug interrupted | Not recovered/ Not resolved |
| US154A-0002 | 40/B | Malaise | 3 | Not related | Drug interrupted | Not recovered/ Not resolved |
| US154A-0002 | 40/B | Disease progression | 5 | Not related | Not applicable | Fatal |
| US185A-0002 | 40/B | Febrile neutropenia | 3 | Not related | Dose not changed | Recovered/ Resolved |
| US185A-0002 | 40/B | Sepsis | 3 | Not related | Dose not changed | Recovering/ Resolving |
| JP002A-0003 | 60/B | Malignant neoplasm progression | 5 | Not related | Dose not changed | Fatal |
| JP007A-0002 | 60/B | Disease progression | 3 | Not related | Drug withdrawn | Not recovered/ Not resolved |
| JP007A-0002 | 60/B | Sepsis | 4 | Not related | Not applicable | Recovered/ Resolved |

*1The patient had hypomagnesaemia at the time of the QTc that was corrected.

*2The patient had Grade 4 pneumonia on 1 Jan. 2023 and passed away due to this AE. Grade 4 pneumonia and Grade 5 pneumonia are separately reported per CRF completion guideline, these are one continuous event.

Example 2: Pharmacokinetic Evaluation of the Present Compound

In the present test of the present compound, PK samples have been collected in up to 24 patients dosed in dose groups of 40, 80, 100, and 120 mg BID Arm A, and in dose groups of 40 and 60 mg BID Arm B (Table 6). Large preliminary PK inter-patient variability was observed.

In Arm A, a trend of dose-related increased in exposures was observed in the dose levels evaluated to date (40 mg, 80 mg, 100 mg, 120 mg BID). In Arm B, the current data was from 40 mg to 60 mg BID to assess dose-dependency in drug exposure. Mean plasma $t_{1/2}$ (when available) ranged from 2.82 to 5.64 hours in Arm A and from 2.61 to 7.29 hours in Arm B, with relatively fast absorption and $T_{max}$ reached within 2 hours post dose. Comparing exposures from Cycle 2 Day 1 to those from Cycle 1 Day 1, minimal to no drug accumulation was observed with repeat dosing.

The impact of concomitant azole anti-fungal medications on the present compound exposure has been evaluated. Based on the available PK data summarized in Table 6, exposures ($C_{max}$ and $AUC_{last}$) at 40 mg BID/Arm B were similar levels as 40 mg BID/Arm A. Additionally, exposures at 60 mg BID/Arm B were close to those observed at 40 mg BID/Arm A. The exposure levels were variable and the sample sizes at each dose level were small, limiting the ability to draw conclusions at this point in the trial. However, the PK data to date in Arm B compared with Arm A suggested that azoles do not have a large or dramatic impact on the exposure of the present compound.

TABLE 6

| Cycle 1 Day 1 (C1D1) | | | | | Cycle 2 Day 1 (C2D1) | | | | |
|---|---|---|---|---|---|---|---|---|---|
| Dose (mg BID)/ Arm (N) | $t_{1/2}$ (hr) | $T_{max}$ (hr) | $C_{max}$ (ng/ mL) | $AUC_{last}$ (hr*ng/ mL) | Dose (mg BID)/ Arm (N) | $t_{1/2}$ (hr) | $T_{max}$ (hr) | $C_{max}$ (ng/ mL) | $AUC_{last}$ (hr*ng/ mL) |
| 40/A (2) | 3.35 | 1.25 | 1164 | 3917 | 40/A (1) | 4.57 | 2 | 772 | 4713 |
| 80/A (4) | 2.82 (±1.13) | 1.25 (±0.87) | 1616 (±1115) | 5149 (±2297) | 80/A (2) | 3.4 | 0.75 | 1400 | 2895 |
| 100/A (2) | 5.64 | 3 | 1380 | 4937 | 100/A (1) | 2.88 | 1 | 2840 | 6059 |
| 120/A (6) | 2.87 (±1.01) | 1.25 (±0.61) | 2275 (±1427) | 6251 (±4869) | 120/A (6) | 3.26 (±1.73) | 1.20 (±0.76) | 1980 (±913) | 7858 (±5606) |
| 40/B (4) | 4.41 (±1.80) | 0.625 (±0.25) | 976 (±797) | 3269 (±3717) | 40/B (2) | 7.29 | 1.25 | 987 | 5334 |
| 60/B (6) | 2.61 (±0.78) | 1.08 (±0.74) | 1166 (±862) | 4143 (±3347) | 60/B (4) | 3.19 (±0.24) | 0.75 (±0.29) | 703 (±441) | 2611 (±1652) |

Mean (±standard deviation). In 40 mg BID/Arm A cohort, n of 2 patients with available PK on C1D1 and 1 on C2D1. In 80 mg BID/Arm A cohort, n of 4 on C1D1 and 2 on C2D1. In 100 mg BID/Arm A cohort, n of 2 on C1D1 and 1 on C2D1. In 120 mg BID/Arm A cohort, n of 6 on C1D1 and C2D1. In 40 mg BID/Arm B cohort, n of 4 on C1D1 and 2 on C2D1. In 60 mg BID/Arm B cohort, n of 6 on C1D1 and 4 on C2D1.

Example 3: Evaluation of the Present Compound Efficacy

In the present test, signs of clinical activity have been observed, including decreases and normalization of bone marrow blasts, elimination of blasts in peripheral blood, and responses according to European LeukemiaNet 2017 Response Criteria. A patient with MLLr assigned to 120 mg BID in Arm A achieved MLFS (morphologic leukemia-free state), while a patient with MLLr assigned to 60 mg BID with azoles in Arm B achieved CRh (complete remission with partial hematological recovery) and CRi (complete remission with incomplete hematologic recovery). Substantial changes in several biomarkers have also been observed, including decreases in HOXA9, PBX3, and MEIS1, and increases in CD11b. These changes have been particularly notable in patients with MLLr or NPM1m.

Example 4: Patient Enrollment (1) At the data cut-off date, a total of 43 patients with acute leukemia have been enrolled in the Phase 1 dose escalation part of the present study at dose levels of 40-200 mg BID in Arm A (n=23) and 40-200 mg in Arm B (n=20). Baseline characteristics are described in Table 7.

TABLE 7

| Baseline characteristics | Arm A (n = 23) | Arm B (n = 20) | Overall (n = 43) |
|---|---|---|---|
| Age (years) | | | |
| Median | 63.0 | 67.5 | 65.0 |
| Min, Max | 24, 84 | 20, 85 | 20, 85 |
| <65 years | 12 (52.2) | 8 (40.0) | 20 (46.5) |
| >=65 years | 11 (47.8) | 12 (60.0) | 23 (53.5) |
| Sex, n (%) | | | |
| Female | 12 (52.2) | 10 (50.0) | 22 (51.2) |
| Male | 11 (47.8) | 10 (50.0) | 21 (48.8) |
| Diagnosis, n (%) | | | |
| AML | 21 (91.3) | 19 (95.0) | 40 (93.0) |
| ALL | 1 (4.3) | 0 | 1 (2.3) |
| MPAL | 1 (4.3) | 1 (5.0) | 2 (4.7) |

TABLE 7-continued

| Baseline characteristics | Arm A (n = 23) | Arm B (n = 20) | Overall (n = 43) |
|---|---|---|---|
| Clinical setting of Leukemia, n (%) | | | |
| De novo | 10 (43.5) | 12 (60.0) | 22 (51.2) |
| Secondary (Treatment-related) | 2 (8.7) | 3 (15.0) | 5 (11.6) |
| Secondary (Transformation from prior heme malignancy) | 6 (26.1) | 3 (15.0) | 9 (20.9) |
| Unknown | 3 (13.0) | 0 | 3 (7.0) |
| ELN2017 risk stratification by genetics, n (%) | | | |
| Favorable | 3 (13.0) | 3 (15.0) | 6 (14.0) |
| Intermediate | 3 (13.0) | 4 (20.0) | 7 (16.3) |
| Adverse | 11 (47.8) | 7 (35.0) | 18 (41.9) |
| Indeterminate | 0 | 1 (5.0) | 1 (2.3) |
| Unknown | 4 (17.4) | 3 (15.0) | 7 (16.3) |
| # prior treatments, n (%) | | | |
| Median | 2.0 | 2.5 | 2.0 |
| Min, Max | 1, 9 | 1, 6 | 1, 9 |
| Prior Transplant, n (%) | | | |
| Yes | 7 (30.4) | 7 (35.0) | 14 (32.6) |
| Prior Venetoclax, n (%) | | | |
| Yes | 16 (69.6) | 14 (70.0) | 30 (69.8) |
| Prior other Menin inhibitors, n (%) | | | |
| Yes | 1 (4.3) | 1 (5.0) | 2 (4.7) |
| Genetics, n (%) | | | |
| NPM1m | 4 (17.4) | 5 (25.0) | 9 (20.9) |
| MLLr | 6 (26.1) | 11 (55.0) | 17 (39.5) |
| other documented mutations | | | |
| ASXL1 | 4 (17.4) | 4 (20.0) | 8 (18.6) |
| FLT3 | 2 (8.7) | 2 (10.0) | 4 (9.3) |
| NUP98 | 2 (8.7) | 1 (5.0) | 3 (7.0) |

TABLE 7-continued

| Baseline characteristics | Arm A (n = 23) | Arm B (n = 20) | Overall (n = 43) |
|---|---|---|---|
| RUNX1 | 4 (17.4) | 2 (10.0) | 6 (14.0) |
| SETBP1 | 0 | 1 (5.0) | 1 (2.3) |
| Bone marrow blast (%) at baseline | | | |
| Median | 60.0 | 64.0 | 61.0 |
| Min, Max | 2.0, 98.0 | 15.0, 90.0 | 2.0, 98.0 |

(2) At the data cut-off date, a total of 57 patients with acute leukemia have been enrolled in the Phase 1 dose escalation part of the present study at dose levels of 40-300 mg BID in Arm A (n=27) and 40-300 mg in Arm B (n=30). Baseline characteristics are described in Table 8.

TABLE 8

| Baseline characteristics | Arm A (n = 27) | Arm B (n = 30) | Overall (n = 57) |
|---|---|---|---|
| Age (years) | | | |
| Median | 63.0 | 67.5 | 65.0 |
| Min, Max | 24, 84 | 20, 85 | 20, 85 |
| <65 years | 15 (55.6) | 16 (53.3) | 31 (54.4) |
| >=65 years | 12 (44.4) | 14 (46.7) | 26 (45.6) |
| Sex, n (%) | | | |
| Female | 16 (59.3) | 17 (56.7) | 33 (57.9) |
| Male | 11 (40.7) | 13 (43.3) | 24 (42.1) |
| Diagnosis, n (%) | | | |
| AML | 24 (88.9) | 29 (96.7) | 53 (93.0) |
| ALL | 2 (7.4) | 0 (0.0) | 2 (3.5) |
| MPAL | 1 (3.7) | 1 (3.3) | 2 (3.5) |
| Clinical setting of Leukemia, n (%) | | | |
| De novo | 14 (51.9) | 21 (70.0) | 35 (61.4) |
| Secondary (Treatment-related) | 5 (18.5) | 5 (16.7) | 10 (17.5) |
| Secondary (Transformation from prior heme malignancy) | 7 (25.9) | 2 (6.7) | 9 (15.8) |
| Unknown | 1 (3.7) | 2 (6.7) | 3 (5.3) |
| ELN2017 risk stratification by genetics, n (%) | | | |
| Favorable | 3 (11.1) | 5 (16.7) | 8 (14.0) |
| Intermediate | 6 (22.2) | 8 (26.7) | 14 (24.6) |
| Adverse | 15 (55.6) | 13 (43.3) | 28 (49.1) |
| Indeterminate | 0 (0.0) | 2 (6.7) | 2 (3.5) |
| Unknown | 0 (0.0) | 1 (3.3) | 1 (1.8) |
| Missing | 3 (11.1) | 1 (3.3) | 4 (7.0) |
| # prior treatments, n (%) | | | |
| Median | 3.00 | 3.00 | 3.00 |
| Min, Max | 1.0, 9.0 | 1.0, 7.0 | 1.0, 9.0 |
| Prior Transplant, n (%) | | | |
| Yes | 8 (29.6) | 11 (36.7) | 19 (33.3) |
| Prior Venetoclax, n (%) | | | |
| Yes | 23 (85.2) | 27 (90.0) | 50 (87.7) |
| Prior other Menin inhibitors, n (%) | | | |
| Yes | 1 (3.7) | 2 (6.7) | 3 (5.3) |

TABLE 8-continued

| Baseline characteristics | Arm A (n = 27) | Arm B (n = 30) | Overall (n = 57) |
|---|---|---|---|
| Genetics, n (%) | | | |
| NPM1m | 5 (18.5) | 9 (30.0) | 14 (24.6) |
| MLLr | 9 (33.3) | 15 (50.0) | 24 (42.1) |
| None Detected | 1 (3.7) | 0 (0.0) | 1 (1.8) |
| Other Mutations | 17 (63.0) | 17 (56.7) | 34 (59.6) |
| ASXL1 | 4 (14.8) | 4 (13.3) | 8 (14.0) |
| CEBPA | 1 (3.7) | 3 (10.0) | 4 (7.0) |
| FLT3 | 1 (3.7) | 6 (20.0) | 7 (12.3) |
| FLT3T | 1 (3.7) | 1 (3.3) | 2 (3.5) |
| NUP98FUS | 2 (7.4) | 2 (6.7) | 4 (7.0) |
| RUNX1 | 5 (18.5) | 2 (6.7) | 7 (12.3) |
| SETBP1 | 0 (0.0) | 1 (3.3) | 1 (1.8) |
| TP53 | 1 (3.7) | 1 (3.3) | 2 (3.5) |
| Other | 13 (8.1) | 14 (46.7) | 27 (47.4) |
| Bone marrow blast (%) at baseline | | | |
| Median | 52.00 | 72.00 | 62.30 |
| Min, Max | 2.0, 98.0 | 5.0, 93.0 | 2.0, 98.0 |

(3) At the time of data cut off, 81 patients (31 patients in Arm A and 50 patients in Arm B) were enrolled. The median age was 57.1 years (range 20-89), 56.8% were female, and 93.8% had AML. The median number of prior lines of therapy was 3 (range 1 to 9). 23 patients (28.4%) had prior allogeneic stem cell transplant, 63 patients (77.8%) had prior venetoclax, and 5 patients (6.2%) had received a prior menin inhibitor. Documented MLLr was reported in 42 pts (51.9%) and NPM1m in 20 (24.7%).

Example 5: Safety Evaluation of the Present Compound (1) No DLTs have been observed at any dose level of 40-200 mg. Majority of the TEAEs were Grade 1 or Grade 2 and managed with supportive care. No drug-related AE has resulted in permanent treatment discontinuation and no treatment-related deaths were observed in the study. Refer to Table 9 for a tabulation of TEAEs in ≥20% of patients regardless of causality, and Table 10 for a tabulation of all TEAEs related to the present compound in ≥2 patients. Treatment-related QT interval prolongation events were not reported. One case of suspected differentiation syndrome has been reported related to the present compound that occurred in a patient with TP-53 mutation, but no cases of differentiation syndrome have occurred in patients with MLLr or NPM1m.

TABLE 9

| Preferred Term | Total (N = 43) |
|---|---|
| Nausea | 15 (34.9%) |
| Vomiting | 10 (23.3%) |
| Fatigue | 10 (23.3%) |
| Hypokalaemia | 9 (20.9%) |

TABLE 10

| Preferred Term* | Total (N = 43) |
|---|---|
| Vomiting | 4 (9.3%) |
| Nausea | 3 (7.0%) |
| Decreased appetite | 3 (7.0%) |

*One patient experienced differentiation syndrome not included due to cut-off ≥2 patients The test in (1) above was further continued and the following results were obtained.

(2) No DLT have been observed at any dose level of 40-300 mg BID. TEAEs assessed as related to the present compound in ≥10% were vomiting (15.5%) and nausea (12.1%). Grade >3 TEAEs in ≥10% included pneumonia (17.2%), sepsis & febrile neutropenia (15.5% each), anemia (13.8%), and platelet count decrease (12.1%), all assessed as unrelated to study drug. Possible differentiation syndrome (DS) was documented in 3 pts: Two patients interrupted treatment, no patients discontinued, and there was no mortality from DS. One patient reported related asymptomatic Grade 3 QT prolongation in the presence of other QT prolonging drugs requiring temporary interruption and subsequent dose reduction with no recurrence.

(3) Among 57 patients, no DLTs have been observed at any dose level of 40-300 mg. No drug-related AE has resulted in permanent treatment discontinuation and no treatment-related deaths were observed in the study. Table 11 shows treatment related TEAEs in 210% of patients. Refer to Tables 12 and 13 for a tabulation of non-hematological or hematological TEAEs in ≥10% of patients regardless of causality. Table 14 shows non-hematological laboratory changes in ≥10% of patients. Differentiation syndrome (DS) was reported in 3 patients; none of them leads to permanent treatment discontinuation. No DS prophylaxis used when starting treatment. Some patients showed hematologic differentiation without significant systemic symptoms, thus these were not assessed as DS.

TABLE 11

Treatment related adverse events in ≥10% of patients (N = 57)

| Preferred Term | Any Grade | Grade ≥3 |
|---|---|---|
| Nausea | 10 (17.5%) | 1 (1.8%) |
| Vomiting | 7 (12.3%) | 1 (1.8%) |

TABLE 12

Non-hematological treatment emergent adverse events (TEAEs) ≥10% regardless of causality (N = 57)

| Preferred Term | Any Grade | Grade ≥3 |
|---|---|---|
| Nausea | 23 (40.4%) | 4 (7.0%) |
| Vomiting | 20 (35.1%) | 3 (5.3%) |
| Decreased appetite | 15 (26.3%) | 2 (3.5%) |
| Headache | 15 (26.3%) | 0 (0.0%) |
| Dyspnoea | 13 (22.8%) | 3 (5.3%) |
| Constipation | 11 (19.3%) | 1 (1.8%) |
| Sepsis | 11 (19.3%) | 10 (17.5%) |
| Stomatitis | 11 (19.3%) | 0 (0.0%) |
| Fatigue | 10 (17.5%) | 1 (1.8%) |
| Diarrhoea | 10 (17.5%) | 0 (0.0%) |
| Epistaxis | 10 (17.5%) | 1 (1.8%) |
| Pneumonia | 10 (17.5%) | 10 (17.5%) |
| Pyrexia | 9 (15.8%) | 0 (0.0%) |
| Muscular weakness | 9 (15.8%) | 2 (3.5%) |
| Oedema peripheral | 9 (15.8%) | 0 (0.0%) |
| Dizziness | 8 (14.0%) | 0 (0.0%) |
| Pain in extremity | 8 (14.0%) | 1 (1.8%) |
| Back pain | 8 (14.0%) | 1 (1.8%) |
| Hypertension | 8 (14.0%) | 3 (5.3%) |
| Electrocardiogram QT prolonged | 7 (12.3%) | 2 (3.5%) |
| Hypotension | 7 (12.3%) | 2 (3.5%) |
| Cough | 7 (12.3%) | 0 (0.0%) |
| Myalgia | 6 (10.5%) | 0 (0.0%) |
| Arthralgia | 6 (10.5%) | 1 (1.8%) |

TABLE 12-continued

Non-hematological treatment emergent adverse events (TEAEs) ≥10% regardless of causality (N = 57)

| Preferred Term | Any Grade | Grade ≥3 |
|---|---|---|
| Haemorrhage intracranial | 6 (10.5%) | 4 (7.0%) |
| COVID-19 | 6 (10.5%) | 3 (5.3%) |
| Dysgeusia | 6 (10.5%) | 0 (0.0%) |

TABLE 13

Hematological treatment emergent adverse events (TEAEs) ≥10% regardless of causality (N = 57)

| Preferred Term | Any Grade | Grade ≥3 |
|---|---|---|
| Febrile neutropenia | 12 (21.1%) | 12 (21.1%) |
| Leukocytosis | 10 (17.5%) | 4 (7.0%) |
| Anaemia | 9 (15.8%) | 8 (14.0%) |
| Platelet count decreased | 9 (15.8%) | 8 (14.0%) |
| Neutrophil count decreased | 7 (12.3%) | 6 (10.5%) |

TABLE 14

Non-hematological laboratory changes ≥10% regardless of causality (N = 57)

| Preferred Term | Any Grade | Grade ≥3 |
|---|---|---|
| Hypokalemia | 34 (7.0%) | 10 (17.2%) |
| AST increase | 23 (40.4%) | 1 (1.8%) |
| ALT increase | 28 (49.1%) | 0 (0.0%) |
| Hypophosphatemia | 19 (33.3%) | 11 (19.3%) |
| Hyponatremia | 32 (56.1%) | 0 (0.0%) |
| Hypocalcemia | 33 (57.9%) | 2 (3.5%) |
| Hypomagnesemia | 26 (4.6%) | 1 (1.8%) |
| Hypertriglyceridemia | 45 (7.9%) | 4 (7.0%) |

(4) At the time of data cut off, the dose level was escalated from 40 mg BID to 300 mg BID (n=81) with no DLT observed. TEAE assessed as related to the compound in ≥10% of patients were vomiting (14.8%) and nausea (12.3%). Grade 3 nausea and vomiting were reported in 1 patient. TEAE in ≥20% of patients regardless of relationship included nausea (37.0%), vomiting (29.6%), febrile neutropenia (22.2%), and decreased appetite, diarrhea, and hypokalemia (21.0% each). There were no reports of grade ≥3 QTc prolongation related to the compound. Grade 1 QTc prolongation was reported in 2 patients (2.4%) and grade 2 in 2 patients (2.4%). Possible differentiation syndrome was reported in 9 patients (11.1%).

Figure 2:
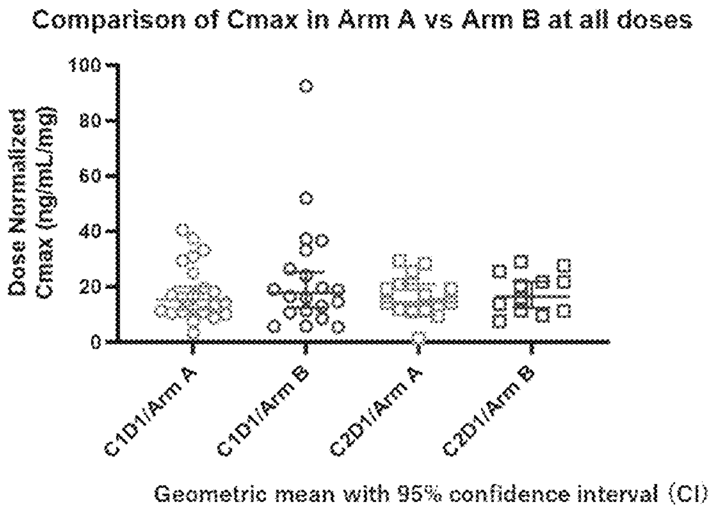
FIG. 2 shows comparison of $C_{max}$ in Arm A and Arm B at all doses.
Figure 3:
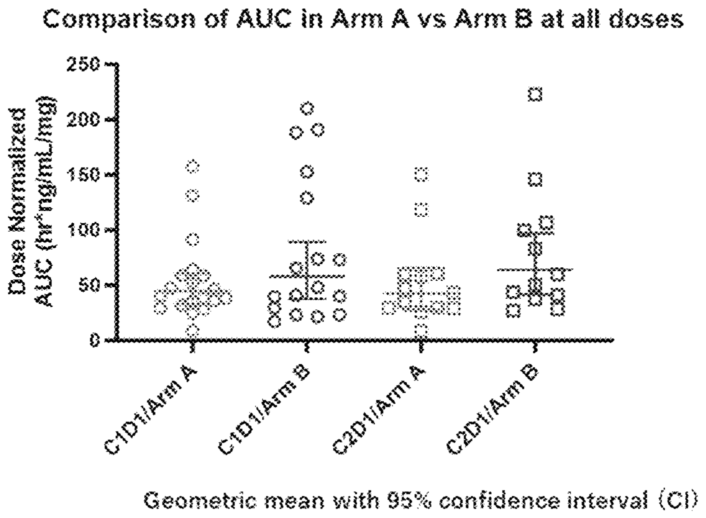
FIG. 3 shows comparison of AUC in Arm A and Arm B at all doses.
Figure 4A:
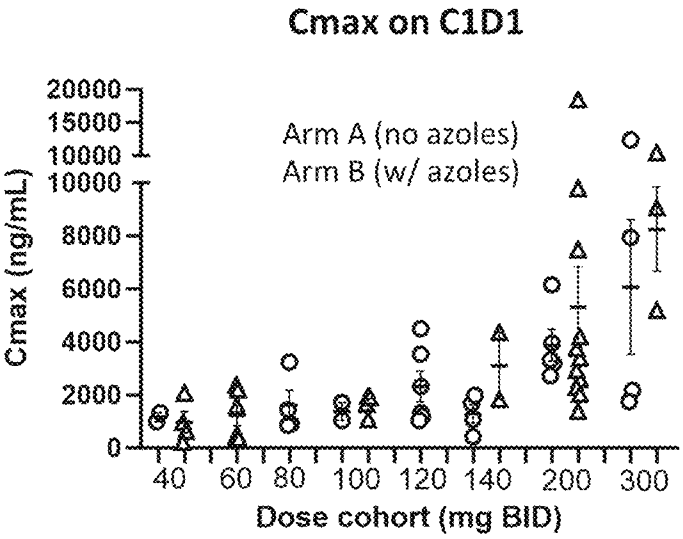
FIG. 4A to 4D show pharmacokinetics data as of data cut off in Example 6.
Figure 4B:
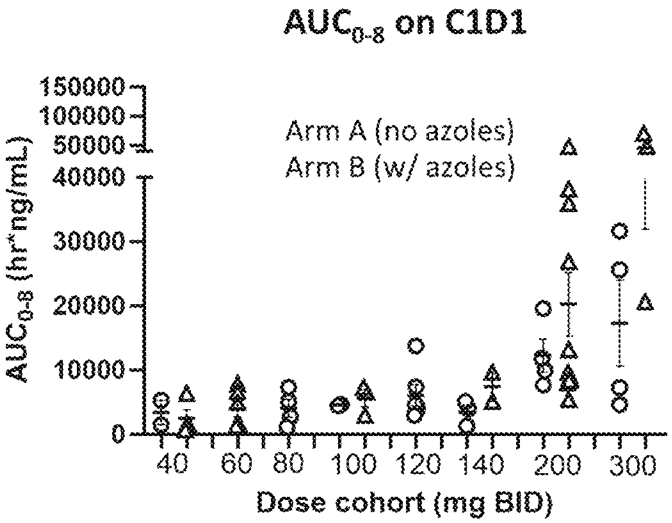
Figure 4C:
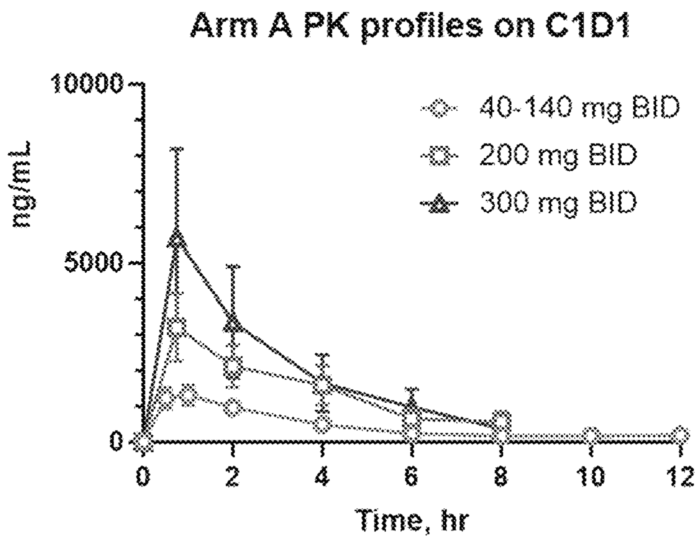
Figure 4D:
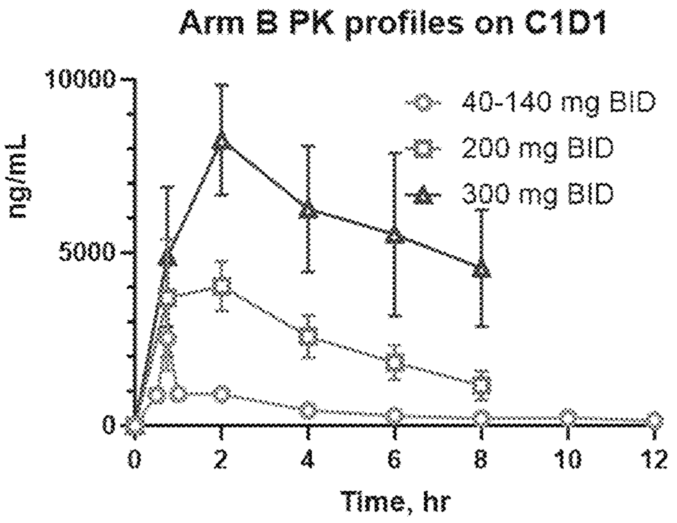

Example 6: Pharmacokinetic Evaluation of the Present Compound (1) In the present study, PK samples have been collected in up to 42 patients dosed in dose groups of 40, 80, 100, 120, 140 and 200 mg BID Arm A, and in dose groups of 40, 60, 100, and 200 mg BID Arm B (Table 15). Mean apparent half-life ranged from ~2 to ~5 hours in Arm A and from ~3 to ~7 hours in Arm B. Absorption was rapid with the maximum concentration within 2 hours of dosing. Dose-dependent increases in exposures were observed, with minimal drug accumulation with repeat dosing. The data to date suggests that azoles do not have a large effect on the exposure of the present compound (FIG. 2, FIG. 3).

TABLE 15

| Cycle 1 Day 1 | | | Cycle 2 Day 1 | | |
|---|---|---|---|---|---|
| Dose (mg BID)/Arm (N) | $C_{max}$ (ng/mL) | $AUC_{last}$ (hr*ng/mL) | Dose (mg BID)/Arm (N) | $C_{max}$ (ng/mL) | $AUC_{last}$ (hr*ng/mL) |
| 40/A(2) | 1164 | 3960 | 40/A(1) | 772 | 4726 |
| 80/A(4) | 1616 (±1115) | 5107 (±2234) | 80/A(2) | 1400 | 2895 |
| 100/A(2) | 1380 | 4937 | 100/A(1) | 2840 | 6059 |
| 120/A(6) | 2323 (±1422) | 6287 (±4847) | 120/A(6) | 1980 (±913) | 7970 (±5833) |
| 140/A(6)* | 1480 (±674) | 3570 (±1427) | 140/A(5)* | 1674 (±1218) | 4204 (±2046) |
| 200/A(4) | 3850 (±1555) | 9653 (±2083) | 200/A(0) | | |
| 40/B(4) | 976 (±797) | 3269 (±3717) | 40/B(2) | 987 | 5334 |
| 60/B(6) | 1166 (±862) | 4238 (±3503) | 60/B(4) | 751 (±384) | 2693 (±1571) |
| 100/B(4) | 1648 (±408) | 5602 (±2340) | 100/B(4) | 1813 (±670) | 8346 (±4957) |
| 200/B(6) | 6260 (±6290) | 21208 (±17313) | 200/B(2) | 4355 | 16658 |

TABLE 15-continued

Mean (±standard deviation),
N = # of patients
*PK from two patients with MDS were included in statistical analysis.

The test in (1) above was further continued and the following results were obtained.

(2) In the present study, PK samples have been collected in patients dosed in dose groups of 40, 80, 100, 120, 140, 200, and 300 mg BID Arm A, and in dose groups of 40, 60, 100, 200, and 300 mg BID Arm B (Table 16). Mean apparent half-life ranged from ~2 to ~4 hours in Arm A and from ~3 to ~7 hours in Arm B. Absorption was rapid with the maximum concentration within 2 hours of dosing. Dose-dependent increases in exposures were observed, with minimal drug accumulation with repeat dosing. The data to date suggests that azoles do not have a large effect on the exposure of the present compound.

TABLE 16

| Cycle 1 Day 1 | | | Cycle 2 Day 1 | | |
|---|---|---|---|---|---|
| Dose (mg BID)/Arm (N) | $C_{max}$ (ng/mL) | $AUC_{last}$ (hr*ng/mL) | Dose (mg BID)/Arm (N) | $C_{max}$ (ng/mL) | $AUC_{last}$ (hr*ng/mL) |
| 40/A (2) | 1164 | 3960 | 40/A (1) | 772 | 4726 |
| 80/A (4) | 1616 (±1115) | 5107 (±2234) | 80/A (2) | 1400 | 2895 |
| 100/A (2) | 1380 | 4937 | 100/A (1) | 2840 | 6059 |
| 120/A (6) | 2323 (±1422) | 6287 (±4847) | 120/A (6) | 1980 (±913) | 7970 (±5833) |
| 140/A (6#) | 1480 (±674) | 3570 (±1427) | 140/A (5#) | 1674 (±1218) | 4204 (±2046) |
| 200/A (5) | 3872 (±1347) | 12128 (±5235) | 200/A (3) | 3850 (±1499) | 11989 (±2138) |
| 300/A (4) | 6068 (±5078) | 15915 (±11856) | 300/A (3) | 3057 (±1766) | 12399 |
| 40/B (4) | 976 (±797) | 3269 (±3717) | 40/B (2) | 987 | 5334 |
| 60/B (6) | 1166 (±862) | 4238 (±3503) | 60/B (4) | 751 (±384) | 2693 (±1571) |
| 100/B (4) | 1648 (±408) | 5602 (±2340) | 100/B (4) | 1813 (±670) | 8346 (±4957) |
| 140/B (2) | 3095 | 6999 | 140/B (1) | 1770 | 5521.00 |
| 200/B (11) | 5699 (±5136) | 21190 (±14439) | 200/B (5*) | 4074 (±2062) | 16777 (±7537) |
| 300/B (3$) | 5973 (±2782) | 25990 (±19856) | 300/B (1$) | 4210 | 20534 |

Mean (±standard deviation).
N = # of patients.
#PK from two MDS patients was included in statistical analysis with one pt exlcuded due to abnormally low drug levels.
*JP034A-0001, US053A-0005, and US185A-0015 at 200 mg BID/Arm B were excluded from C2D1 PK analysis. US053A-0005 pharmacophobia with missing pills. JP034A-0001 abnormal levels as if no drug taken on C2D1. US185A-0015 had 2 missing PK tps.
$US158A-0007 C1D1 pending re-assay, US017A-0003 C2D1 pending re-assay.

(3) FIGS. 4A to 4D show pharmacokinetics data as of data cut off. Mean $t_{1/2}$ ranged from 2-6 hrs in Arm A (without azole) and 3-7 hrs in Arm B (with azole). Dose-related increases in exposures observed at doses ≥140 mg BID, minimal accumulation with repeat dosing. Pharmacokinetic data thus far has not identified large drug-drug interaction (>~2-fold) with azoles.

Figure 5:
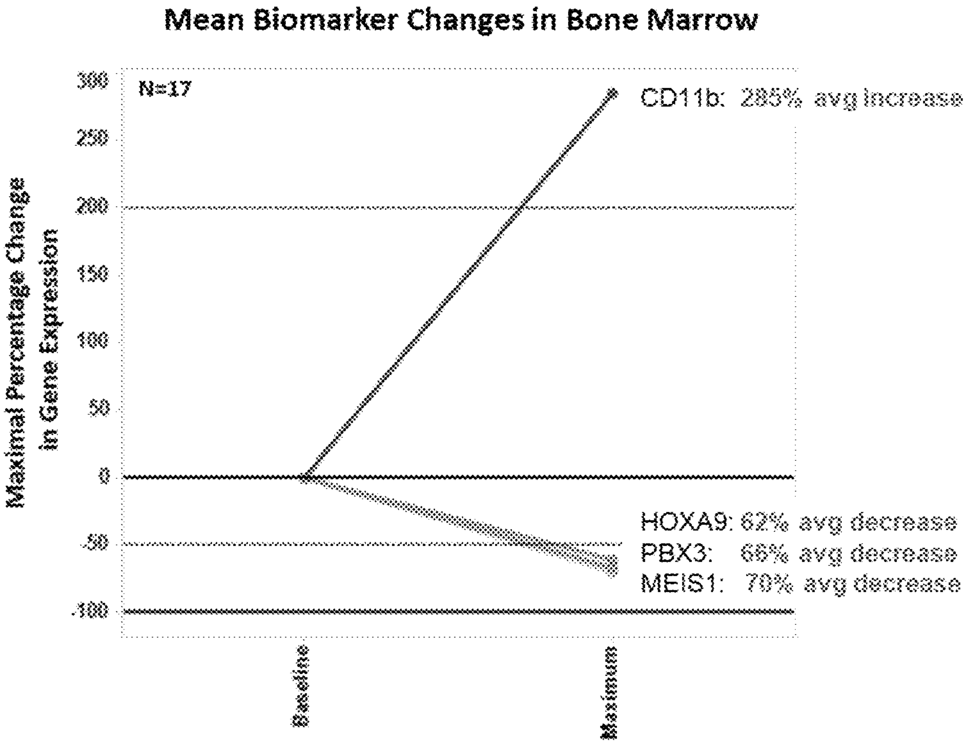
FIG. 5 shows maximum percentage change in gene expression of leukemic (HOXA9, MEIS1, PBX3) and differentiation (CD11b) biomarkers in bone marrow aspirate of patients with MLLr or NPM1m AML for whom a baseline and post-baseline sample were collected. All dose levels and time points are combined.

Example 7: Pharmacodynamic Evaluation of the Present Compound (1) FIG. 5 shows average of the maximum percentage change of gene expression of leukemic (HOXA9, MEIS1, PBX3) and differentiation (CD11b) biomarkers in bone marrow aspirate of patients with MLLr or NPM1m AML for whom a baseline and post-baseline sample were collected. All dose levels and time points are combined. Clear decreases in HOXA9, PBX3, and MEIS1, and increases in CD11b were observed.

Figure 6A:
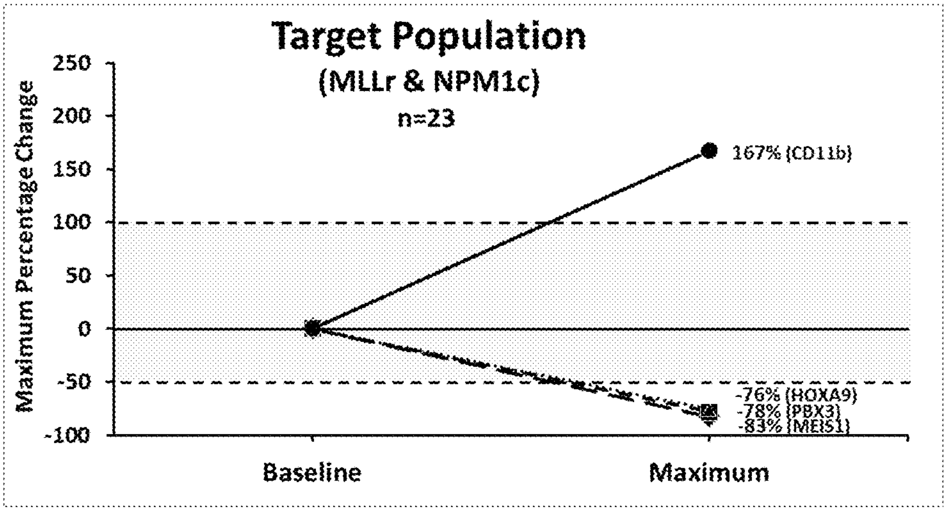
FIGS. 6A and 6B show average of the maximum percentage change of gene expression of leukemic (HOXA9, MEIS1, PBX3) and differentiation (CD11b) biomarkers in bone marrow aspirate of patients from all dose levels, for whom a baseline and post-baseline sample were collected.
Figure 6B:
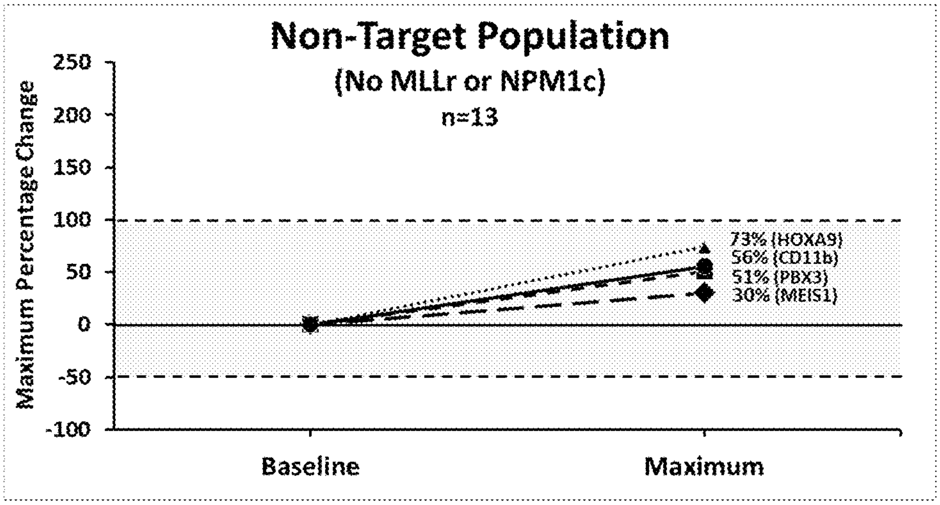

(2) FIGS. 6A and 6B show average of the maximum percentage change of gene expression of leukemic (HOXA9, MEIS1, PBX3) and differentiation (CD11b) biomarkers in bone marrow aspirate of patients from all dose levels, for whom a baseline and post-baseline sample were collected. Clear decreases in HOXA9, PBX3, and MEIS1, and increases in CD11b were observed in patients with target mutations.

Figure 7A:
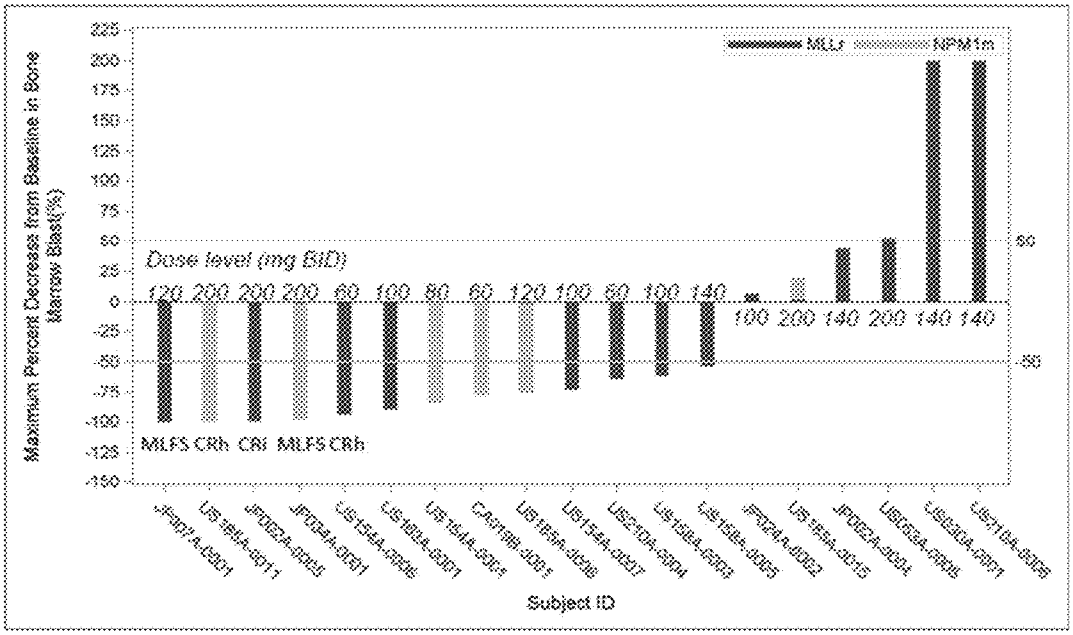
FIGS. 7A and 7B show maximum percentage decrease from baseline in bone marrow blast (%).

Example 8: Clinical Activity Evaluation of the Present Compound (1) Of 43 patients enrolled, 17 patients had MLLr and 9 patients had NPM1m, with 19 evaluable at the time of data extraction and 5 responders per ELN 2017 (FIG. 7A). At 200 mg BID in Arm B, 4 evaluable patients had MLLr or NPM1m (n=1 and 3, respectively) and 1 patient achieved CRh/CRi, 1 patient achieved CRi, and 1 patient achieved MLFS. Two additional patients with MLLr also achieved response per ELN2017 at lower dose levels (CRh/CRi and MLFS).

The test in (1) above was further continued and the following results were obtained.

Figure 7B:
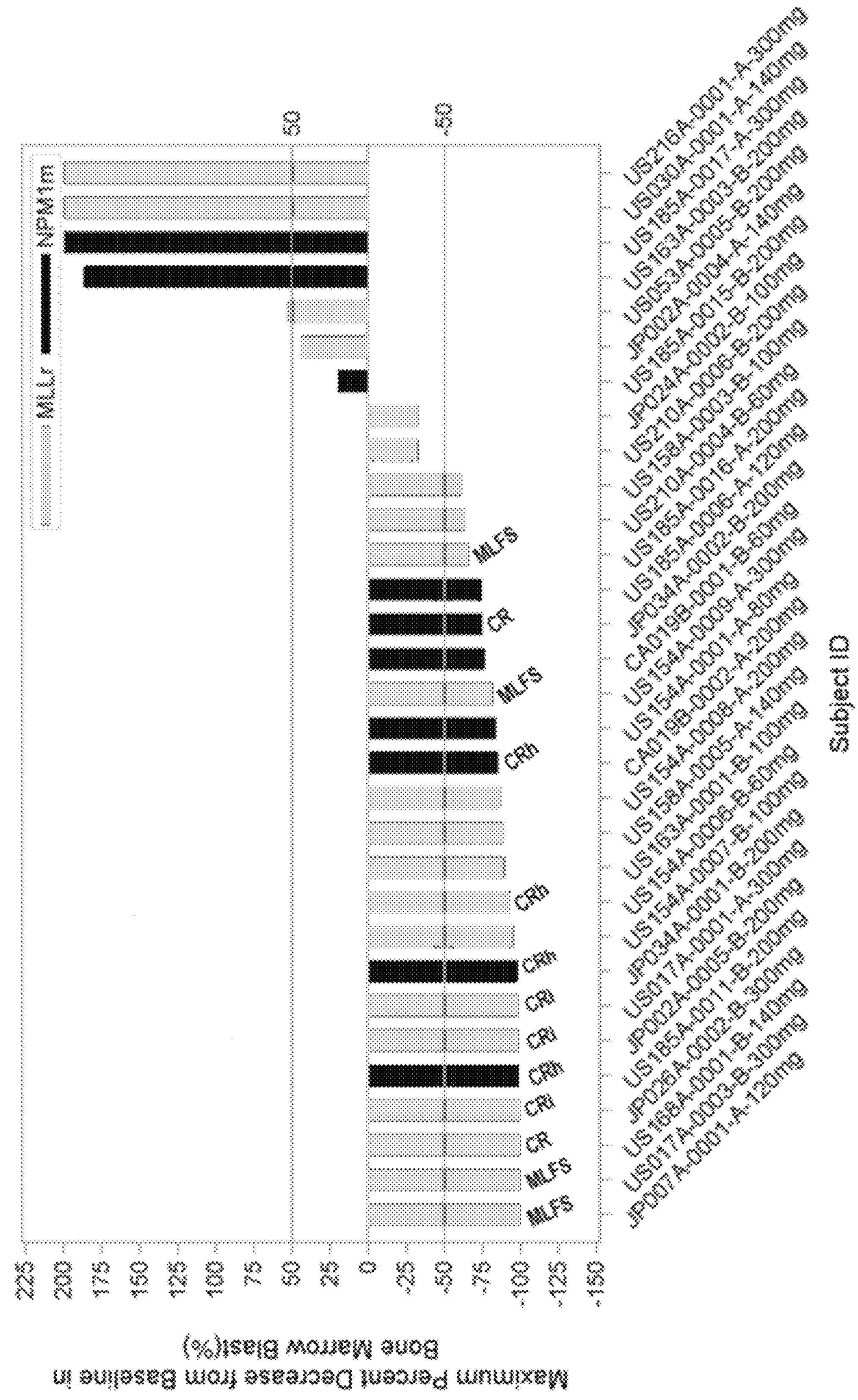

(2) Of 58 patients, 26 patients had MLLr and 14 patients had NPM1m. Among all patients with MLLr or NPM1m treated at ≥140 mg BID who were prior menin inhibitor naïve and finished 1 cycle (n=22), ORR (CR+CRi+MLFS) was 45% (10/22) and the CR+CRh rate was 23% (5/22). Across all dose levels (40 mg BID to mg 300 BID) in prior menin inhibitor naïve pts with MLLr or NPM1m and finished 1 cycle, the ORR and CR+CRh were 32% (12/38) and 16% (6/38), respectively (FIG. 7B).

Figure 8:
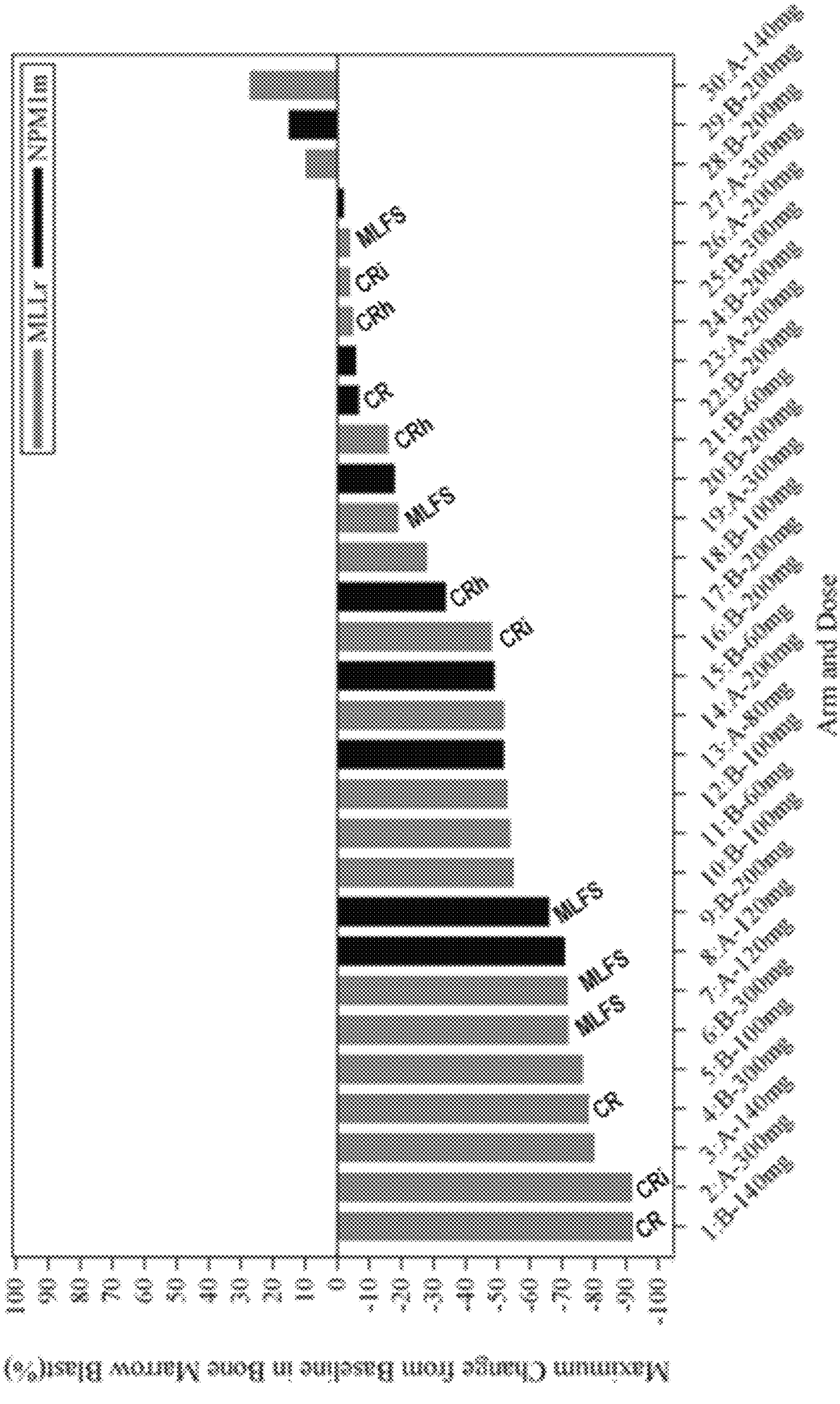
FIG. 8 shows maximum percentage decrease from baseline in bone marrow blast (%).

(3) Bone marrow blast reduction was observed in patients with MLLr or NPM1m (FIG. 8). Among patients enrolled in ≥140 mg BID, 12 patients with MLLr and 9 patients with NPM1m were evaluable at the time of data cut off. Table 17 shows responses by ELN2017 criteria. CR+CRh was 17% (2/12 patients) and Objective Response Rate (ORR; CR+CRh+CRi+MLFS) was 67% (8/12 patients) in patients with MLLr. CR+CRh was 33% (3/9 patients) and ORR was 44% (4/9 patients) in patients with NPM1m.

TABLE 17

| Responses by ELN 2017 | MLLr ≥ 140 mg BID n = 12 | NPM1m ≥ 140 BID mg n = 9 | MLLr + NPM1m ≥ 140 mg BID n = 21 |
|---|---|---|---|
| Objective Response Rate | 8 (67%) | 4 (44%) | 12 (57%) |
| Composite CR | 5 (42%) | 3 (33%) | 7 (33%) |
| CR + CRh | 2 (17%) | 3 (33%) | 5 (24%) |

(4) At the time of data cut off, 35 patients with MLLr or NPM1m who had not received a prior menin inhibitor were treated with active doses of the compound (≥140 mg BID in Arm A or Arm B). Among the 22 pts with MLLr (20 AML, 2 ALL), the objective response rate (ORR) by ELN 2017 (CR+CRi+MLFS) was 59.1% (13/22) with CR+CRh achieved in 22.7% (5/22). Among the 13 patients with NPM1m AML, the ORR was 53.8% (7/13) and CR+CRh achieved in 23.1% (3/13). Among patients with other menin-sensitizing genetics, 1 patient (AML) with a CALM-AF10 fusion also achieved a CR. Overall, the median time to objective response and to CR+CRh was 1.0 and 1.0 months, respectively.

Example 9: Evaluation Test of Combination Drug Efficacy Against Cell Proliferation MOLM-13 cells and OCI-AML3 cells were obtained from DSMZ (Deutsche Sammlung von Mikroorganismen und Zellkulturen GmbH). MOLM-13 cells were cultured in RPMI 1640 medium containing 20% fetal bovine serum and 1% penicillin/streptomycin at 37° C. in the presence of 5% $CO_2$. OCI-AML3 cells were cultured in MEM Alpha medium containing 20% fetal bovine serum and 1% penicillin/streptomycin at 37° C. in the presence of 5% $CO_2$.

MOLM-13 cells were seeded at 1600 cells per well in a 96-well plate, and the present compound was added to the plate at a final concentration of 7.8 to 250 nmol/L. Then, venetoclax, azacitidine, cytarabine, daunorubicin, or gilteritinib were added to the plate at final concentrations of 3.9 to 125 nmol/L, 313 to 10000 nmol/L, 7.8 to 250 nmol/L, 0.78 to 25 nmol/L, and 3.9 to 125 nmol/L, respectively. The plate was cultured for 7 days.

OCI-AML3 cells were seeded at 1600 cells per well in a 96-well plate, and the present compound was added to the plate at a final concentration of 7.8 to 250 nmol/L. Then, venetoclax, azacitidine, cytarabine, or daunorubicin were added to the plate at final concentrations of 156 to 5000 nmol/L, 313 to 10000 nmol/L, 313 to 10000 nmol/L, and 0.78 to 25 nmol/L, respectively. The plate was cultured for 7 days.

After the culture was completed, the cell viability was calculated using PrestoBlue™ Cell Viability Reagent (Invitrogen, A13261). The combination Index (CI) was calculated based on the cell viability software (manufactured by Biosoft).

TABLE 18

| MOLM-13 | | | |
|---|---|---|---|
| Compound ratio | CI | | |
| (the present compound:venetoclax) | $ED_{50}$ | $ED_{75}$ | $ED_{90}$ |
| 1:2 | 1.54 | 1.12 | 0.82 |
| 1:1 | 1.01 | 0.78 | 0.61 |
| 1:0.5 | 0.80 | 0.61 | 0.48 |
| 1:0.25 | 0.80 | 0.57 | 0.42 |
| 1:0.125 | 0.67 | 0.51 | 0.39 |

TABLE 19

| MOLM-13 | | | |
|---|---|---|---|
| Compound ratio | CI | | |
| (the present compound:azacitidine) | $ED_{50}$ | $ED_{75}$ | $ED_{90}$ |
| 1:160 | 0.79 | 0.54 | 0.38 |
| 1:80 | 0.77 | 0.52 | 0.37 |
| 1:40 | 0.68 | 0.48 | 0.35 |
| 1:20 | 1.03 | 0.71 | 0.51 |
| 1:10 | 0.71 | 0.63 | 0.57 |

TABLE 20

| MOLM-13 | | | |
|---|---|---|---|
| Compound ratio | CI | | |
| (the present compound:cytarabine) | $ED_{50}$ | $ED_{75}$ | $ED_{90}$ |
| 1:4 | 1.26 | 1.06 | 0.91 |
| 1:2 | 1.04 | 0.89 | 0.79 |
| 1:1 | 0.86 | 0.72 | 0.63 |
| 1:0.5 | 0.90 | 0.69 | 0.56 |
| 1:0.25 | 0.82 | 0.65 | 0.54 |

TABLE 21

| MOLM-13 | | | |
|---|---|---|---|
| Compound ratio | CI | | |
| (the present compound:daunorubicin) | $ED_{50}$ | $ED_{75}$ | $ED_{90}$ |
| 1:0.4 | 1.32 | 1.17 | 1.06 |
| 1:0.2 | 0.99 | 0.88 | 0.83 |
| 1:0.1 | 0.85 | 0.75 | 0.71 |
| 1:0.05 | 1.00 | 0.78 | 0.66 |
| 1:0.025 | 0.96 | 0.82 | 0.75 |

TABLE 22

| MOLM-13 | | | |
|---|---|---|---|
| Compound ratio | CI | | |
| (the present compound:gilteritinib) | $ED_{50}$ | $ED_{75}$ | $ED_{90}$ |
| 1:2 | 0.89 | 0.89 | 0.90 |
| 1:1 | 0.98 | 0.94 | 0.93 |
| 1:0.5 | 0.82 | 0.79 | 0.79 |
| 1:0.25 | 0.83 | 0.73 | 0.68 |
| 1:0.125 | 0.59 | 0.60 | 0.65 |

TABLE 23

| OCI-AML3 | | | |
|---|---|---|---|
| Compound ratio | CI | | |
| (the present compound:venetoclax) | $ED_{50}$ | $ED_{75}$ | $ED_{90}$ |
| 1:80 | 0.68 | 0.17 | 0.05 |
| 1:40 | 0.64 | 0.16 | 0.05 |
| 1:20 | 0.61 | 0.15 | 0.04 |
| 1:10 | 0.46 | 0.27 | 0.19 |
| 1:5 | 0.52 | 0.42 | 0.40 |

TABLE 24

| OCI-AML3 | | | |
|---|---|---|---|
| Compound ratio | CI | | |
| (the present compound:azacitidine) | $ED_{50}$ | $ED_{75}$ | $ED_{90}$ |
| 1:160 | 0.68 | 0.37 | 0.32 |
| 1:80 | 0.73 | 0.31 | 0.26 |
| 1:40 | 0.73 | 0.30 | 0.29 |
| 1:20 | 0.58 | 0.49 | 1.09 |
| 1:10 | 1.16 | 0.76 | 1.23 |

TABLE 25

| OCI-AML3 | | | |
|---|---|---|---|
| Compound ratio | CI | | |
| (the present compound:cytarabine) | $ED_{50}$ | $ED_{75}$ | $ED_{90}$ |
| 1:160 | 0.92 | 0.87 | 0.82 |
| 1:80 | 0.86 | 0.79 | 0.74 |
| 1:40 | 0.77 | 0.71 | 0.69 |
| 1:20 | 0.79 | 0.65 | 0.59 |
| 1:10 | 0.69 | 0.61 | 0.62 |

TABLE 26

| OCI-AML3 | | | |
|---|---|---|---|
| Compound ratio | CI | | |
| (the present compound:daunorubicin) | $ED_{50}$ | $ED_{75}$ | $ED_{90}$ |
| 1:0.4 | 1.57 | 1.13 | 0.99 |
| 1:0.2 | 1.56 | 0.99 | 0.87 |
| 1:0.1 | 1.52 | 0.86 | 0.75 |
| 1:0.05 | 1.93 | 1.21 | 1.20 |
| 1:0.025 | 3.11 | 1.95 | 1.89 |

In the test to evaluate the efficacy of combination drugs against cell proliferation, it was found that the present compound exhibits an excellent cell proliferation inhibitory effect on MOLM-13 cells when used in combination with venetoclax, azacitidine, cytarabine, daunorubicin, or gilteritinib. On OCI-AML3 cells, it was found that the present compound exhibits an excellent cell proliferation inhibitory effect when used in combination with venetoclax, azacitidine, or cytarabine.

Example 10: Evaluation Test of Combination Drug Efficacy Using Tumor-Bearing Mice Transplanted with MOLM-13 Cells The antitumor effects of the present compound, venetoclax, and azacitidine were evaluated. The present compound was weighed and dissolved in 0.5 w/v % Methyl Cellulose 400 solution to give the compound concentrations of 20 mg/mL and 10 mg/mL. Venetoclax was weighed and suspended in a mixed solution of Phosal 50 propylene glycol (60%)/Polyethylene glycol-400 (30%)/Ethanol (10%) to give the compound concentration of 5 mg/mL. Azacitidine was weighed and dissolved in saline to give the compound concentration of 0.3 mg/mL.

MOLM-13 cells (DSMZ) were intradermally implanted around the ventral region of 5-week old NOD. CB17-PrkdcSCID/J mice (female, The Jackson Laboratory Japan) at $1\times10^6$ cells/mouse. After confirming the engraftment of MOLM-13 cells 7 days after the transplantation, the present compound was orally administered to the mice at a dose of 100 mg/kg or 200 mg/kg, and venetoclax was orally administered to the mice at a dose of 50 mg/kg, once a day for 15 days. Azacitidine was intraperitoneally administered to the mice once a day for 5 days at a dose of 3 mg/kg. The tumor volume was measured over time from the start of the administration, and the reduction effect of the tumor volume due to the compound-administration was evaluated. The tumor volume was calculated by the following formula using short axis and long axis of the tumor measured with an electronic caliper (Mitutoyo).

$$\text{Tumor volume } [\text{mm}^3] = 0.5 \times (\text{short axis [mm]})^2 \times \text{long axis [mm]}$$

The control administration group in which only the solvent was administered and the test substance administration group were compared, and T/C was calculated using the following formula to evaluate the antitumor effect.

$$T/C\ (\%) = (\text{Tumor volume at the end of administration in the test substance administration group} - \text{Tumor volume at the start of administration in the test substance administration group}) / (\text{Tumor volume at the end of administration in the control administration group} - \text{Tumor volume at the start of administration in the control administration group}) \times 100$$

Table 27 shows the T/C (%) of tumor-bearing mice transplanted with MOLM-13 cells in each test.

TABLE 27

| Test | Administration route | Dose (mg/kg) | Administration period (day) | T/C (%) |
|---|---|---|---|---|
| the present compound | oral | 100 | 15 | 22.6 |
| the present compound | oral | 200 | 15 | 8.4 |
| venetoclax and azacitidine | oral and intraperitoneal | 50 and 3 | 15 and 5 | 36.1 |
| the present compound, venetoclax, and azacitidine | oral, oral, and intraperitoneal | 100, 50, and 3 | 15, 15, and 5 | 2.4 |
| the present compound, venetoclax, and azacitidine | oral, oral, and intraperitoneal | 200, 50, and 3 | 15, 15, and 5 | −2.6 |

In the combination efficacy evaluation test using tumor-bearing mice, it was found that the present compound exhibits excellent antitumor effects when used in combination with venetoclax and azacitidine.

Example 11: Evaluation Test of Combination Drug Efficacy Using Tumor-Bearing Mice Transplanted with MOLM-13 Cells The antitumor effects of the present compound, cytarabine, and daunorubicin were evaluated. The present compound was weighed and dissolved in 0.5 w/v % Methyl Cellulose 400 solution to give the compound concentrations of 20 mg/mL and 10 mg/mL. Cytarabine (Cylocide Injection 200 mg/10 mL, Nippon Shinyaku Co., Ltd.) was diluted with saline (Otsuka Saline Injection, Otsuka Pharmaceutical Factory Co., Ltd.) to 8 mg/mL. Daunorubicin (Daunomycin for injection 20 mg, Meiji, Seika Pharma Co., Ltd.) was dissolved in saline (Otsuka Saline Injection, Otsuka Pharmaceutical Factory Co., Ltd.) to 0.2 mg/mL.

MOLM-13 cells (DSMZ) were intradermally implanted around the ventral region of 8-week old NOD. CB17-PrkdcSCID/J mice (female, The Jackson Laboratory Japan) at $1\times10^6$ cells/mouse. After confirming the engraftment of MOLM-13 cells 6 days after the transplantation, the present compound was orally administered to the mice at a dose of 100 mg/kg or 200 mg/kg once a day for 17 days. Cytarabine was intraperitoneally administered to the mice at a dose of 80 mg/kg once a day for 5 days. Daunorubicin was intravenously administered to the mice at a dose of 1 mg/kg once a day for 3 days. The tumor volume was measured over time from the start of the administration, and the reduction effect of the tumor volume due to the compound-administration was evaluated. The tumor volume was calculated by the following formula using short axis and long axis of the tumor measured with an electronic caliper (Mitutoyo).

$$\text{Tumor volume } [\text{mm}^3] = 0.5 \times (\text{short axis [mm]})^2 \times \text{long axis [mm]}$$

The control administration group in which only the solvent was administered and the test substance administration group were compared, and T/C was calculated using the following formula to evaluate the antitumor effect.

$$T/C\ (\%) = (\text{Tumor volume at the end of administration in the test substance administration group} - \text{Tumor volume at the start of administration in the test substance administration group}) / (\text{Tumor volume at the end of administration in the control administration group} - \text{Tumor volume at the start of administration in the control administration group}) \times 100$$

Table 28 shows the T/C (%) of tumor-bearing mice transplanted with MOLM-13 cells in each test.

TABLE 28

| Test | Administration route | Dose (mg /kg) | Administration period (day) | T/C (%) |
|---|---|---|---|---|
| the present compound | oral | 100 | 17 | 29.8 |
| the present compound | oral | 200 | 17 | 0.3 |
| cytarabine and daunorubicin | intraperitoneal and intravenous | 80 and 1 | 5 and 3 | 80.4 |
| the present compound, cytarabine, and daunorubicin | oral, intraperitoneal, and intravenous | 100, 80, and 1 | 17, 5, and 3 | 12.5 |
| the present compound, cytarabine, and daunorubicin | oral, intraperitoneal, and intravenous | 200, 80, and 1 | 17, 5, and 3 | −0.5 |

In the combination efficacy evaluation test using tumor-bearing mice, it was found that the present compound exhibits excellent antitumor effects when used in combination with cytarabine and daunorubicin.

Example 12: Evaluation Test of Combination Drug Efficacy Using Tumor-Bearing Mice Transplanted with MOLM-13 Cells The antitumor effects of the present compound and gilteritinib were evaluated. The present compound was weighed and dissolved in 0.5 w/v % Methyl Cellulose 400 solution to give the compound concentrations of 20 mg/mL and 10 mg/mL. Gilteritinib was weighed and suspended in 0.5 w/v % Methyl Cellulose 400 solution to give the compound concentrations of 3 mg/mL.

MOLM-13 cells (DSMZ) were intradermally implanted around the ventral region of 5-week old NOD. CB17-PrkdcSCID/J mice (female, The Jackson Laboratory Japan) at $1\times10^6$ cells/mouse. After confirming the engraftment of MOLM-13 cells 6 days after the transplantation, the present compound was orally administered to the mice at a dose of 100 mg/kg or 200 mg/kg, and gilteritinib was orally administered to the mice at a dose of 30 mg/kg, once a day for 18 days. The tumor volume was measured over time from the start of the administration, and the reduction effect of the tumor volume due to the compound-administration was evaluated. The tumor volume was calculated by the following formula using short axis and long axis of the tumor measured with an electronic caliper (Mitutoyo).

$$\text{Tumor volume } [\text{mm}^3] = 0.5 \times (\text{short axis [mm]})^2 \times \text{long axis [mm]}$$

The control administration group in which only the solvent was administered and the test substance administration group were compared, and T/C was calculated using the following formula to evaluate the antitumor effect.

$$T/C\ (\%) = \frac{(\text{Tumor volume at the end of administration in the test substance administration group} - \text{Tumor volume at the start of administration in the test substance administration group})}{(\text{Tumor volume at the end of administration in the control administration group} - \text{Tumor volume at the start of administration in the control administration group})} \times 100$$

Table 29 shows the T/C (%) of tumor-bearing mice transplanted with MOLM-13 cells in each test.

TABLE 29

| Test | Administration route | Dose (mg /kg) | Administration period (day) | T/C (%) |
|---|---|---|---|---|
| the present compound | oral | 100 | 18 | 43.8 |
| the present compound | oral | 200 | 18 | 1.8 |
| gilteritinib | oral | 30 | 18 | 5.3 |
| the present compound and gilteritinib | oral and oral | 100 and 30 | 18 and 18 | −2.0 |
| the present compound and gilteritinib | oral and oral | 200 and 30 | 18 and 18 | −1.9 |

In the combination efficacy evaluation test using tumor-bearing mice, it was found that the present compound exhibits excellent antitumor effects when used in combination with gilteritinib.

Example 13: Evaluation Test of Combination Drug Efficacy Using Tumor-Bearing Mice Transplanted with OCI-AML3 Cells The antitumor effects of the present compound, venetoclax, and azacitidine were evaluated. The present compound was weighed and dissolved in 0.5 w/v % Methyl Cellulose 400 solution to give the compound concentrations of 20 mg/mL and 10 mg/mL. Venetoclax was weighed and suspended in a mixed solution of Phosal 50 propylene glycol (60%)/Polyethylene glycol-400 (30%)/Ethanol (10%) to give the compound concentration of 5 mg/mL. Azacitidine was weighed and dissolved in saline to give the compound concentration of 0.3 mg/mL.

OCI-AML3 cells (DSMZ) were intradermally implanted around the ventral region of 6-week old NOD. CB17-PrkdcSCID/J mice (female, The Jackson Laboratory Japan) at $1\times10^6$ cells/mouse. After confirming the engraftment of OCI-AML3 cells 11 days after the transplantation, the present compound was orally administered to the mice at a dose of 100 mg/kg or 200 mg/kg, and venetoclax was orally administered to the mice at a dose of 50 mg/kg, once a day for 21 days. Azacitidine was intraperitoneally administered to the mice at a dose of 3 mg/kg once a day for 5 days. The tumor volume was measured over time from the start of the administration, and the reduction effect of the tumor volume due to the compound-administration was evaluated. The tumor volume was calculated by the following formula using short axis and long axis of the tumor measured with an electronic caliper (Mitutoyo).

$$\text{Tumor volume } [mm^3] = 0.5 \times (\text{short axis [mm]})^2 \times \text{long axis [mm]}$$

The control administration group in which only the solvent was administered and the test substance administration group were compared, and T/C was calculated using the following formula to evaluate the antitumor effect.

$$T/C\ (\%) = \frac{(\text{Tumor volume at the end of administration in the test substance administration group} - \text{Tumor volume at the start of administration in the test substance administration group})}{(\text{Tumor volume at the end of administration in the control administration group} - \text{Tumor volume at the start of administration in the control administration group})} \times 100$$

Table 30 shows the T/C (%) of tumor-bearing mice transplanted with OCI-AML3 cells in each test.

TABLE 30

| Test | Administration route | Dose (mg/kg) | Administration period (day) | T/C (%) |
|---|---|---|---|---|
| the present compound | oral | 100 | 21 | 47.1 |
| the present compound | oral | 200 | 21 | 34.3 |
| venetoclax and azacitidine | oral and intraperitoneal | 50 and 3 | 21 and 5 | 48.7 |
| the present compound, venetoclax, and azacitidine | oral, oral, and intraperitoneal | 100, 50, and 3 | 21, 21, and 5 | 14.7 |
| the present compound, venetoclax, and azacitidine | oral, oral, and intraperitoneal | 200, 50, and 3 | 21, 21, and 5 | 7.2 |

In the combination efficacy evaluation test using tumor-bearing mice, it was found that the present compound exhibits excellent antitumor effects when used in combination with venetoclax and azacitidine.

Example 14: Evaluation Test of Combination Drug Efficacy Using Tumor-Bearing Mice Transplanted with OCI-AML3 Cells The antitumor effects of the present compound, cytarabine, and daunorubicin were evaluated. The present compound was weighed and dissolved in 0.5 w/v % Methyl Cellulose 400 solution to give the compound concentrations of 20 mg/mL and 10 mg/mL. Cytarabine (Cylocide Injection 200 mg/10 mL, Nippon Shinyaku Co., Ltd.) was diluted with saline (Otsuka Saline Injection, Otsuka Pharmaceutical Factory Co., Ltd.) to 8 mg/mL. Daunorubicin (Daunomycin for injection 20 mg, Meiji, Seika Pharma Co., Ltd.) was dissolved in saline (Otsuka Saline Injection, Otsuka Pharmaceutical Factory Co., Ltd.) to 0.2 mg/mL.

OCI-AML3 cells (DSMZ) were intradermally implanted around the ventral region of 7-week old NOD. CB17-PrkdcSCID/J mice (female, The Jackson Laboratory Japan) at $1\times10^6$ cells/mouse. After confirming the engraftment of OCI-AML3 cells 11 days after the transplantation, the present compound was orally administered to the mice at a dose of 100 mg/kg or 200 mg/kg once a day for 21 days. Cytarabine was intraperitoneally administered to the mice at a dose of 80 mg/kg once a day for 5 days. Daunorubicin was intravenously administered to the mice at a dose of 1 mg/kg once a day for 3 days. The tumor volume was measured over time from the start of the administration, and the reduction effect of the tumor volume due to the compound-administration was evaluated. The tumor volume was calculated by the following formula using short axis and long axis of the tumor measured with an electronic caliper (Mitutoyo).

$$\text{Tumor volume } [\text{mm}^3] = 0.5\times(\text{short axis [mm]})^2\times\text{long axis [mm]}$$

The control administration group in which only the solvent was administered and the test substance administration group were compared, and T/C was calculated using the following formula to evaluate the antitumor effect.

$$T/C\ (\%) = $$

(Tumor volume at the end of administration in the test substance administration group −

Tumor volume at the start of administration in the test substance administration group)/

-continued (Tumor volume at the end of administration in the control administration group −

Tumor volume at the start of administration in the control administration group) × 100

Table 31 shows the T/C (%) of tumor-bearing mice transplanted with OCI-AML3 cells in each test.

TABLE 31

| Test | Administration route | Dose (mg /kg) | Administration period (day) | T/C (%) |
|---|---|---|---|---|
| the present compound | oral | 100 | 21 | 53.1 |
| the present compound | oral | 200 | 21 | 41.7 |
| cytarabine and daunorubicin | intraperitoneal and intravenous | 80 and 1 | 5 and 3 | 60.9 |
| the present compound, cytarabine, and daunorubicin | oral, intraperitoneal, and intravenous | 100, 80, and 1 | 21, 5, and 3 | 29.4 |
| the present compound, cytarabine, and daunorubicin | oral, intraperitoneal, and intravenous | 200, 80, and 1 | 21, 5, and 3 | 16.2 |

In the combination efficacy evaluation test using tumor-bearing mice, it was found that the present compound exhibits excellent antitumor effects when used in combination with cytarabine and daunorubicin.

Examples 1 to 8 above may be also carried out at a dose of 400 mg/BID, 500 mg/BID, 600 mg/BID, or 700 mg/BID converted to the free form of the present compound.

Reference Example 1: Estimation of Metabolites

Metabolites of the present compound were estimated according to the following protocol.

(i) Sample Information

Human plasma: C1D1, C2D1, 80 mg, BID, time point pre, 0.5, 1, 2, 4, 6, 8, 10, 12 hr (ii) Sample Preparation Plasma sample was pooled by AUC pooling method for 0 to 12 hours. The sample (100 μL) was extracted with three volumes of ACN (0.1% formic acid in 1:4 MeOH/ACN) and centrifuged for 5 min at 13,000 rpm. The supernatant (350 μL) was transferred to a 96 well plate and dried down to 100 μL for analysis.

(iii) Data Processing

The LC/MS full scan data was processed manually, assisted by Metabolynx, to identify the metabolites. Product ion spectra were acquired by a separate UPLC-HRMS/MS run to assign the structures of the metabolites by MS/MS data interpretation.

(iv) Instrumentation

UPLC System: Waters ACQUITY I-Class system (SN's: J14UFL436M, E14BUR170G)

Mass Spectrometer: Waters Xevo G2 XS (SN: YEA499)

(v) UPLC Conditions

Mobile Phase A: 0.1% formic acid in water

Mobile Phase B: 0.1% formic acid in ACN

Gradient: time/% B (0/5, 0.5/5, 8/30, 12/60, 12.3/95, 14.5/95, 14.6/5, 15/5)

HPLC Column: Phenomenex Kinetex Bi-Phenyl, 2.1×100 mm, 2.6 μm

Flow Humane (mL/min): 0.4

Injection Volume (uL): 2

Mass Spec Conditions

Ionization: Positive ESI

Sample cone: 30 V

Capillary: 1.2 KV

Source offset: 80 V

Source temperature: 115° C.

Desolvation gas flow: 500 (L/Hr)

Desolvation temperature: 500°

Reagents

Water: Fisher, Optima LC/MS grade

Acetonitrile: Fisher Optima LC/MS grade

Formic Acid: Fisher Optima LC/MS grade (iv) result

A and B were detected as metabolites of the present compound, whose structures are estimated as follows.

TABLE 32

| Metabolite | Retention time (min) | Structure |
|---|---|---|
| A | 5.90 | 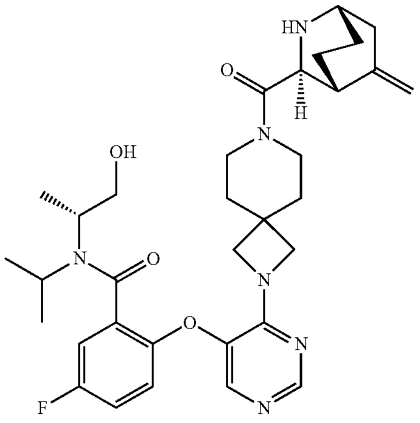<br>compound 1<br>or<br>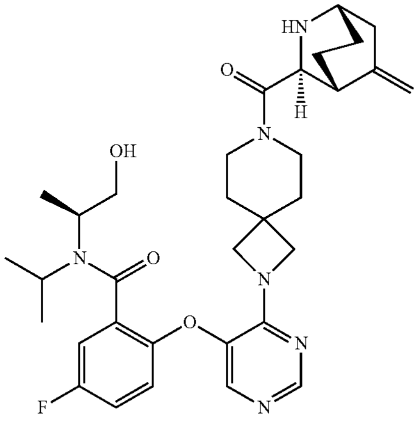<br>compound 2 |
| B | 6.34 | 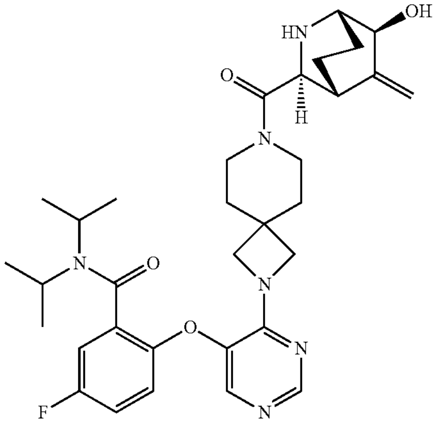<br>compound 3 |

The present compound has been confirmed to be safe at 40 to 300 mg BID (Examples 1 and 5), and clinical results suggesting drug efficacy were obtained at 60 mg BID in Arm B, 120 mg BID in Arm A (Example 3) and 140-300 mg BID in Arm A or B (Example 8). Thus, safety and efficacy can be also ensured at doses of 200 mg BID or more. Furthermore, it has been found that the present compound exhibits a remarkable cell proliferation inhibitory effect when used in combination with venetoclax, azacitidine, cytarabine, daunorubicin, or gilteritinib (Example 9). Especially, for MOLM-13 cells, particularly remarkable tumor growth inhibitory effects were confirmed in "combination of the present compound, venetoclax, and azacitidine", "combination of the present compound, cytarabine, and daunorubicin", and "combination of the present compound and gilteritinib" (Examples 10-12), and for OCI-AML3 cells, particularly remarkable tumor growth inhibitory effects were confirmed in "combination of the present compound, venetoclax, and azacitidine" and "combination of the present compound, cytarabine, and daunorubicin" (Examples 13 and 14).

INDUSTRIAL APPLICABILITY

The medicament disclosed herein comprises an optically active azabicyclo ring derivative or a pharmaceutically acceptable salt thereof, or a hydrate or solvate thereof, which may be used as a medicament for treating or preventing a cancer.

The invention claimed is:

1. A method for treating an acute leukemia comprising:

orally administrating, to a subject in need thereof, a therapeutically effective amount of an active ingredient consisting of 5-fluoro-2-[(4-{7-[(1S,3S;4R)-5-methylidene-2-azabicyclo[2.2.2]octane-3-carbonyl]-2,7-diazaspiro[3.5]nonan-2-yl}pyrimidin-5-yl)oxy]-N,N-di(propan-2-yl)benzamide in free form or a pharmaceutically acceptable salt thereof, or a hydrate or solvate thereof, wherein the subject is a human, wherein one dose of the active ingredient is 200 mg or 300 mg converted to the free form, wherein the active ingredient is administered twice a day, and wherein the acute leukemia is relapsed or refractory acute myeloid leukemia with MLL rearrangement, relapsed or refractory acute lymphoid leukemia with MLL rearrangement or relapsed or refractory acute myeloid leukemia with NPM1 mutation.

2. The method of claim 1, wherein the acute leukemia is relapsed or refractory acute myeloid leukemia with MLL rearrangement.

3. The method of claim 1, wherein the acute leukemia is relapsed or refractory acute lymphoid leukemia with MLL rearrangement.

4. The method of claim 1, wherein the acute leukemia is relapsed or refractory acute myeloid leukemia with NPM1 mutation.

5. The method of claim 1, wherein the acute leukemia is relapsed or refractory acute myeloid leukemia with MLL rearrangement, and one dose of the active ingredient is 300 mg converted to the free form.

6. The method of claim 1, wherein the acute leukemia is relapsed or refractory acute lymphoid leukemia with MLL rearrangement, and one dose of the active ingredient is 300 mg converted to the free form.

7. The method of claim 1, wherein the acute leukemia is relapsed or refractory acute myeloid leukemia with NPM1 mutation, and one dose of the active ingredient is 300 mg converted to the free form.

* * * * *